(12) United States Patent
Sawan et al.

(10) Patent No.: US 7,027,874 B1
(45) Date of Patent: Apr. 11, 2006

(54) BODY ELECTRONIC IMPLANT AND ARTIFICIAL VISION SYSTEM THEREOF

(75) Inventors: Mohamad Sawan, Laval (CA);
Jean-François Harvey, Blainville, CA (US); Martin Roy, Montréal (CA);
Jonathan Coulombe, Montréal (CA);
Yvon Savaria, Montréal (CA); Colince Donfack, Nepean (CA)

(73) Assignee: Polyvalor s.e.c., Montreal (CA)

( * ) Notice: Subject to any disclaimer, the term of this patent is extended or adjusted under 35 U.S.C. 154(b) by 320 days.

(21) Appl. No.: 10/416,403

(22) PCT Filed: Nov. 16, 2000

(86) PCT No.: PCT/CA00/01374
§ 371 (c)(1),
(2), (4) Date: May 12, 2003

(87) PCT Pub. No.: WO02/40095
PCT Pub. Date: May 23, 2002

(51) Int. Cl.
*A61N 1/00* (2006.01)
(52) U.S. Cl. ..................................... 607/116
(58) Field of Classification Search ................. 607/53, 607/116
See application file for complete search history.

(56) References Cited

U.S. PATENT DOCUMENTS

| | | | |
|---|---|---|---|
| 4,551,149 A | 11/1985 | Sciarra | 623/4 |
| 4,628,933 A | 12/1986 | Michelson | 128/419 R |
| 4,969,468 A | 11/1990 | Byers et al. | 128/642 |
| 5,159,927 A | 11/1992 | Schmid | 128/419 R |
| 5,215,088 A | 6/1993 | Normann et al. | 128/642 |
| 5,324,315 A | 6/1994 | Grevious | 607/60 |
| 5,324,316 A | 6/1994 | Schulman et al. | 607/61 |
| 5,499,981 A * | 3/1996 | Kordis | 606/41 |
| 5,800,535 A | 9/1998 | Howard, III | 623/10 |
| 5,807,397 A | 9/1998 | Barreras | 607/61 |
| 5,873,901 A | 2/1999 | Wu et al. | 607/54 |
| 5,876,425 A | 3/1999 | Gord et al. | 607/56 |
| 5,935,155 A | 8/1999 | Humayun et al. | 607/54 |
| 6,035,238 A * | 3/2000 | Ingle et al. | 607/98 |

FOREIGN PATENT DOCUMENTS

GB 2016276 9/1979

OTHER PUBLICATIONS

Campbell, Patrick K. et al., "A Silicon-Based, Three-Dimensional Neural Interface: Manufacturing Processes for an Intracortical Electrode Array", IEEE Trasactions on Biomedical Engineering, 1991, No. 8, New York, US, pp. 758-767.

Jones, Kelly E. et al., "A Multiplexing/Demultiplexing System for use with an Intracortical Electrode Array", IEEE, Department of Bioengineering, University of Utah, Salt Lake City, Utah 84112, Oct. 29, 1992, pp. 1394-1395.

(Continued)

*Primary Examiner*—George Manuel
*Assistant Examiner*—Lenwood Faulcon, Jr.
(74) *Attorney, Agent, or Firm*—Fogg and Associates, LLC; David N. Fogg

(57) ABSTRACT

A miniaturized body electronic implant for providing artificial vision to a blind person or for other uses as neuromuscular sensors and microstimulators. The implant has a high resolution electrode array connected to a chip integrating implant stimulation and monitoring circuits, mounted on the back of the electrode array. The implant is powered by and communicates with an external unit through an inductive bi-directional link.

27 Claims, 19 Drawing Sheets

OTHER PUBLICATIONS

Veraart, C. et al., "Selective Stimulation of the Human Optic Nerve", Neural Rehabilitation Engineering Lab., Belgium, 1999, pp. 57-59.

Stieglitz, T. et al., "A Flexible Retina Implant for People Suffering from Retinitis Pigmentosa", Fraunhofer Institute for Biomedical Engineering, Germany, 1999, pp. 61-64.

"Now, Electronic 'Eyes' for the blind", Science & Technology, Artificial Vision, Business Week, Jan. 31, 2000.

Dobelle, Wm H., "Artificial Vision for the Blind by Connecting a Television Camera to the Visual Cortex", ASAIO Journal 2000, pp. 3-9.

* cited by examiner

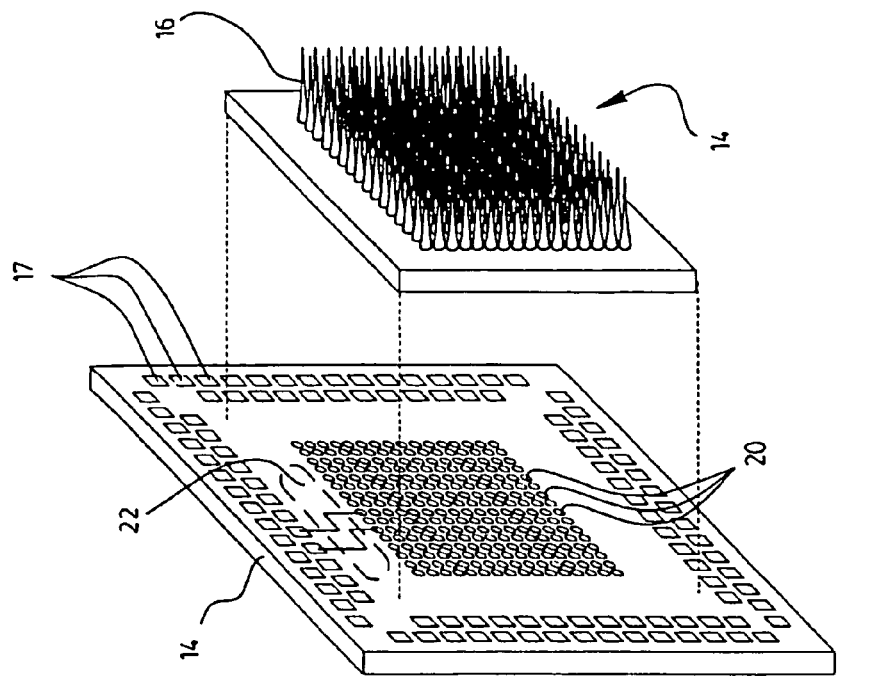
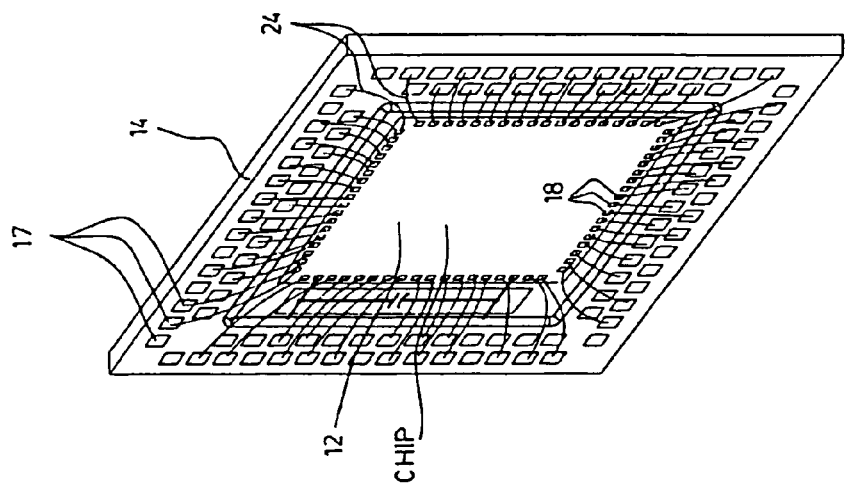
FIG. 3

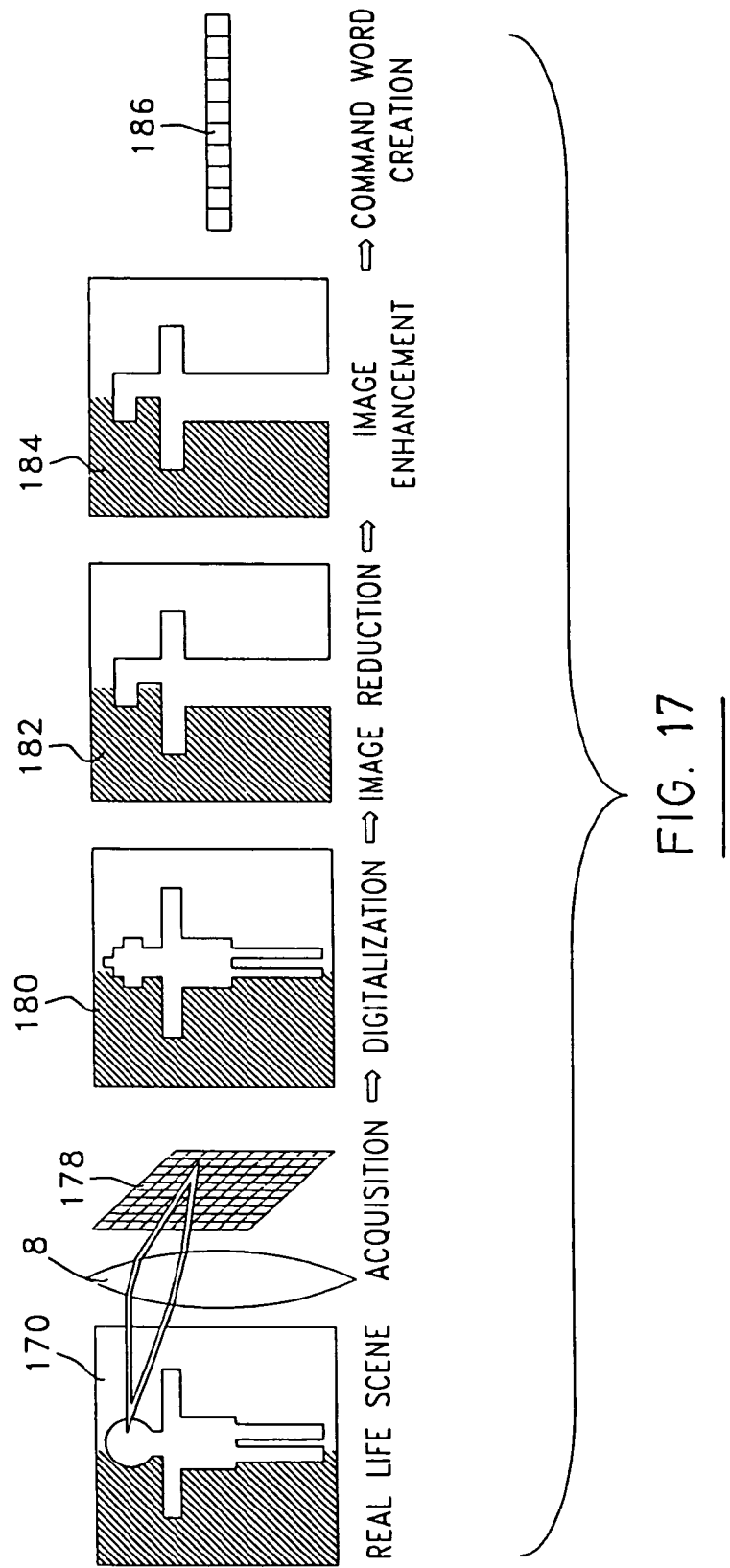

BODY ELECTRONIC IMPLANT AND ARTIFICIAL VISION SYSTEM THEREOF

FIELD OF THE INVENTION

The present invention relates to body electronic implants, and more particularly to a body electronic implant that can be used to stimulate the visual cortex of a blind person for providing artificial vision, or to stimulate other body organs or tissues or nerves for other purposes, and that can also be used as a monitoring instrument for diagnostic purposes.

BACKGROUND

Blindness is still nowadays difficult to cure. Technologies such as speech synthesizers, 3D tactile displays and dedicated scanners improve the quality of life of blind persons by allowing them to read text and manipulate money. However, for seeing., the situation is still the same as a hundred, or even a thousand years ago.

Since electrical stimulation techniques are applied in many circumstances to enhance or restore organ function, a few research teams are working on the recuperation of a limited but functional vision to totally blind persons. A functional vision means that the person will be able to do, without assistance, most of the tasks being part of every day life. It will be limited since no system in the near future will be able to replace the natural vision system with the same accuracy. The required resolution and data processing capabilities are simply too large.

A person is considered legally blind if a visual dysfunction is present and sufficient to greatly affect his everyday life. The medical criterions vary from one country to another but, in general, those who are considered legally blind include a specific group of totally blind persons. This means that they do not see anything and live in a world of complete darkness. The causes of blindness are numerous. Some causes originate in the eye and others are related to the visual pathways.

The history of human visual stimulation began in 1960 when it was found that when a specific part of the human brain was stimulated with an electrical current, a fixed light spot appeared in the visual field of the patient. The part of the brain was later identified as the visual cortex and the light spots are called phosphenes. In 1968, results of clinical experiments related to visual stimulation were first published. The experiments were done with different voltage sources and spacing between electrodes through an array of 81 platinum electrodes. In all cases, the electrical stimulation was done on the surface of the visual cortex. As research progressed, notable discoveries were made and can be summarized as follows: current based intracortical stimulation leads to a significant current reduction, more stable phosphenes and a phosphene intensity that is proportional to the current. To accomplish the visual stimulation, two ma in steps are necessary. The first is to acquire a real life scene and generate stimulation information, or stimulation command words. The second is to inject the proper electrical current to do the stimulation according to the command words.

There are at least three undertaken research activities intended to create adequate vision using electrical stimulation. Each one has its own distinctive characteristics, which are the following:

1) Retina stimulation, where an electrode array is inserted into the light sensitive retina. The advantage of this method is to use most of the natural visual pathway. It is an advantage but also an inconvenience since the visual pathway must be intact and functioning properly. Some of the best challenges of this method of stimulation are mechanical. Since the electrode array is located on the retina, it will be subjected to the very large angular accelerations of the eye. The electrode array must be secured in place very firmly to avoid damaging the retina. Furthermore, to have a good contact with the retina, the electrode array must not be planar but must match the spherical nature of the eye. This approach seems to be dedicated to vision enhancement because the visual pathway is intact. For example, it would be ideal for patients losing the sensitivity of their peripheral vision.

2) Cortical stimulation, where the electrode array is inserted into the brain visual cortex. This method is also dedicated to totally blind persons. Its only requirement is that the visual cortex be intact, which seems to be the case more than 90% of the time. Research is under progress to determine long term stimulation effects on the brain and cell damage due to a high density of electrodes, but the preliminary results are encouraging. A critical step to this method is the insertion of the electrode array into the visual cortex. The current approach suggests a pneumatic system.

3) Optical nerve stimulation is a new stimulation strategy recently introduced. Obviously, the visual pathway must be intact from the optic nerve to the visual cortex. The exact nature of the signals carried by the optic nerve is not thoroughly known and more research is needed before feasibility can be demonstrated.

Known in the art are U.S. Pat. No. 4,551,149 (Sciarra); U.S. Pat. No. 4,628,933 (Michelson); U.S. Pat. No. 5,159,927 (Schmid); U.S. Pat. No. 5,215,088 (Normann et al.); U.S. Pat. No. 5,324,315 (Grevious); U.S. Pat. No. 5,324,316 (Schulman et al.); U.S. Pat. No. 5,876,425 (Gord et al.); U.S. Pat. No. 5,800,535 (Howard, III); U.S. Pat. No. 5,807,397 (Barreras); U.S. Pat. No. 5,873,901 (Wu et al.); U.S. Pat. No. 5,935,155 (Humayun et al.); UK patent application GB 2,016,276 assigned to W H Ross Foundation (Scotland) for Research into Blindness and published on Sep. 26, 1979; and Canadian patent No. 908,750 (Brindley et al.) issued on Aug. 29, 1972, depicting the state of the art.

The above patent documents show that various implants have been designed, at least on a theoretical basis. However, many problems arise when the time comes to put them into practice. Difficulties in the production of electronic implants lay for example in the integration of the various required functions and the miniaturisation of the whole system. The existing implants exhibit high power consumption as they are built using separate electronic modules that further take significant space. The RF part, operating at high speed, is generally made with discrete electronic components due to the electromagnetic interferences generated by this part; it is thus not integrated with the rest of the implant circuit, which would otherwise allow a reduction of the dimensions and the power consumption of the implant. Since an implantable system with discrete components has a high power rating, its power supply by an inductive link is thus hardly practicable. A few designs group the electronics and the electrodes on the same silicon slice. This method facilitates achievement of a vector of a few electrodes, but its application to a large number of electrodes in an array format remains to be proven. The efficiency of an inductive coupling to supply the implantable part of the system is very low because the majority of the currently used techniques are based on ASK modulation. This low efficiency prevents the integration of all the desired functions in the same implant when discrete component designs are used.

The implants used for electric stimulation purposes are thus far unable to monitor changes on the electrode-tissue interface. Such a monitoring function is however highly desired to monitor and follow the evolution of the milieu in contact with the implanted system. The majority of the existing systems are unable to process a large number of inputs and outputs (many tens and hundreds); they are mostly designed for a few stimulation channels only, e.g. for a 10×10 array of electrodes. Furthermore, the assembly of implant electronics with an electrode array having a large number of electrodes in a surface having reduced dimensions has so far not received much attention in the art, as for some other aspects related to implants and implant systems.

SUMMARY

An object of the present invention is to provide a body electronic implant which may be used as a stimulating implant on the visual cortex to provide artificial vision to a blind person, or for other applications such as a monitoring device for implantable biomedical measurements, and especially for measuring parameters around an electrode-neuronal tissues interface.

Another object of the present invention is to provide a body implant which is sufficiently miniaturized and has an integration level adapted for full and direct fitting into the cerebral cortex, at the back of the head of a user, yet which is highly configurable, functionally flexible and has a low power consumption.

Another object of the present invention is to provide a body implant assembly combining a full custom mixed-signal chip and a large number of electrodes fitting on a surface having reduced dimensions.

Another object of the present invention is to provide a body implant capable of storing preset stimulation parameters actively useable with real-time incoming specific stimulation parameters to form the stimulation signals, thereby relieving external unit-implant real-time communications.

Another object of the present invention is to provide a body implant capable of monitoring changes on the electrode-tissue interface through voltage, current and impedance measurements, and capable of reporting these changes to the external unit for diagnosis and adjustment purposes.

Another object of the present invention is to provide an implant system based on the above implant, and which can process real scene images for improved stimulation over an electrode array having a limited resolution.

According to the present invention, there is provided a body implant assembly comprising:
- an electrode array having multiple adjacent electrodes directed towards respective stimulation sites;
- an antenna;
- a full custom mixed-signal chip including a transceiver circuit coupled to the antenna, an AC to DC voltage transformation circuit coupled to the transceiver circuit and powering the full custom mixed-signal chip from energy contained in a control signal received by the transceiver circuit, a controller connected to the transceiver circuit and processing operation data contained in the control signal received by the transceiver circuit, and a stimuli generator circuit connected to the controller and generating stimulation signals in accordance with the operation data;
- an electrode selection circuit connected to the stimuli generator circuit and having selectable outputs for transmission of the stimulation signals to selected ones of the electrodes in accordance with the operation data; and
- a substrate support having a first side receiving the full custom mixed-signal chip, the antenna and the electrode selection circuit, and a second, opposite side receiving the electrode array, the first side having contacts lying around the full custom mixed-signal chip and connected to the outputs of the electrode selection circuit respectively, the second side having an array of adjacent contacts aligned with and connected to the electrodes respectively, the contacts on the first and second sides being interconnected respectively together by an interconnection circuit across the substrate support.

According to the present invention, there is also provided a body implant comprising:
- an electrode array having multiple adjacent electrodes directed towards respective stimulation sites;
- an antenna;
- a transceiver circuit coupled to the antenna;
- an AC to DC voltage transformation circuit coupled to the transceiver circuit and providing implant power supply from energy contained in an implant control signal received by the transceiver circuit;
- a controller connected to the transceiver circuit and processing operation data contained in the implant control signal received by the transceiver circuit;
- a stimuli generator circuit connected to the controller and generating stimulation signals in accordance with the operation data; and
- an electrode selection circuit connected between the stimuli generation circuit and the electrode array, the electrode selection circuit having selectable outputs for transmission of the stimulation signals to selected ones of the electrodes in accordance with the operation data;
- the controller having a deco der circuit decoding the operation data contained in the implant control signal, a configuration controller storing common and specific stimulation parameters specified in the operation data and respectively addressed to all of the stimulation sites and specific ones of the stimulation sites, and a stimulation command controller transmitting stimulation control signals to the stimuli generator circuit in accordance with the common and specific stimulation parameters.

According to the present invention, there is also provided a body implant comprising:
- an electrode array having multiple adjacent electrodes directed towards respective stimulation sites;
- an antenna;
- a transceiver circuit coupled to the antenna;
- an AC to DC voltage transformation circuit coupled to the transceiver circuit and providing implant power supply from energy contained in an implant control signal received by the transceiver circuit;
- a controller connected to the transceiver circuit and processing operation data contained in the implant control signal received by the transceiver circuit;
- a stimuli generator circuit connected to the controller and generating stimulation signals in accordance with the operation data;
- an electrode selection circuit connected between the stimuli generation circuit and the electrode array, the electrode selection circuit having selectable outputs for transmission of the stimulation signals to selected ones of the electrodes in accordance with the operation data; and a monitoring unit coupled between the controller and the electrode selection circuit, and controllably taking signal measurements at selected ones of the stimulation sites in response to monitoring control signals and producing test result signals indicative of the signal measurements;

the controller having a decoder circuit decoding the operation data contained in the implant control signal, a monitoring command generator decoding diagnosis instructions contained in the operation data and transmitting the monitoring control signals to the monitoring unit in accordance with the diagnosis instructions, and a diagnosis controller receiving and processing the test result signals from the monitoring unit.

According to the present invention, there is also provided a body implant comprising:

an electrode array having multiple adjacent electrodes directed towards respective measurement sites;

an antenna;

a transceiver circuit coupled to the antenna;

an AC to DC voltage transformation circuit coupled to the transceiver circuit and providing implant power supply from energy contained in an implant control signal received by the transceiver circuit; a controller connected to the transceiver circuit and processing operation data contained in the implant control signal received by the transceiver circuit;

an electrode selection circuit connected to the electrode array, the electrode selection circuit having selectable outputs for communication with selected ones of the electrodes and the respective measurement sites; and a monitoring unit coupled between the controller and the electrode selection circuit, and controllably taking signal measurements at the selected ones of the measurement sites in response to monitoring control signals and producing test result signals indicative of the signal measurements;

the controller having a decoder circuit decoding the operation data contained in the implant control signal, a monitoring command generator decoding diagnosis instructions contained in the operation data and transmitting the monitoring control signals to the monitoring unit in accordance with the diagnosis instructions, and a diagnosis controller receiving and processing the test result signals from the monitoring unit.

According to the present invention, there is also provided a body implant comprising:

an electrode array having multiple adjacent electrodes directed towards respective stimulation sites; an antenna;

a transceiver circuit coupled to the antenna;

an AC to DC voltage transformation circuit coupled to the transceiver circuit and providing implant power supply from energy contained in an implant control signal received by the transceiver circuit;

a controller connected to the transceiver circuit and processing operation data contained in the implant control signal received by the transceiver circuit; a stimuli generator circuit connected to the controller and generating stimulation signals in accordance with the operation data; and an electrode selection circuit connected between the stimuli generation circuit and the electrode array, the electrode selection circuit having selectable outputs grouped into channels for transmission of the stimulation signals to selected ones of the electrodes in accordance with the operation data;

the electrode selection circuit including, for each channel, a demultiplexer circuit connected to and operating switch arrangements in accordance with site and polarity control signals, the switch arrangements being subjected to the stimulation signals and connected respectively to the outputs assigned to the channel;

the stimuli generator circuit including, for each channel, a signal generator controlled by a channel controller assisted by a timer connected to a register circuit receiving stimulation control signals, the signal generator producing the stimulation signals in accordance with the stimulation control signals, the register circuit and the channel controller producing the site and polarity control signals in accordance with the stimulation control signals; and the controller having a decoder circuit decoding the operation data contained in the implant control signal, a configuration controller storing stimulation parameters specified in the operation data, and a stimulation command controller transmitting the stimulation control signals to the stimuli generator circuit in accordance with the stimulation parameters.

According to the present invention, there is also provided an artificial vision system for stimulating a visual cortex of a blind person, comprising:

a body implant including an electrode array having multiple adjacent electrodes applicable against the visual cortex of the blind person, and a micro-stimulator means mounted on a back side of the electrode array, for selectively generating stimulation signals on the electrodes producing phosphenes on the visual cortex representing an artificial image in response to airwave-received implant control signals; and an external unit including an image sensor adapted to take a real scene image, an image processor and command generator means connected to the image sensor for processing image data signals produced by the image sensor in accordance with predetermined processing operations and generating implant compatible stimulation commands causing the body implant to produce the artificial image on the visual cortex corresponding to the real scene image, and a transceiver circuit connected to the image processor and command generator means, for producing airwave-transmitted implant control signals carrying the stimulation commands, the processing operations including a digitalization of the image data signals to form a digital image, an image reduction of the digital image into a scaled down image having a same resolution as the electrode array, and an image enhancement of the scaled down image to form an enhanced image corresponding to the artificial image produced by the implant unit and from which the stimulation commands are generated.

BRIEF DESCRIPTION OF THE DRAWINGS

A detailed description of preferred embodiments will be given hereinbelow with reference to the following drawings, in which like numbers refer to like elements:

FIGS. 1, 2 and 3 are, respectively, schematic views of front and rear sides of a substrate support of a body implant assembly and an exploded view thereof with an electrode array according to an embodiment of the present invention;

FIG. 17 is a schematic diagram illustrating an image processing sequence performed by an image processor for command word generation for implant control according to the present invention;

DETAILED DESCRIPTION OF THE PREFERRED EMBODIMENTS

Figure 21:
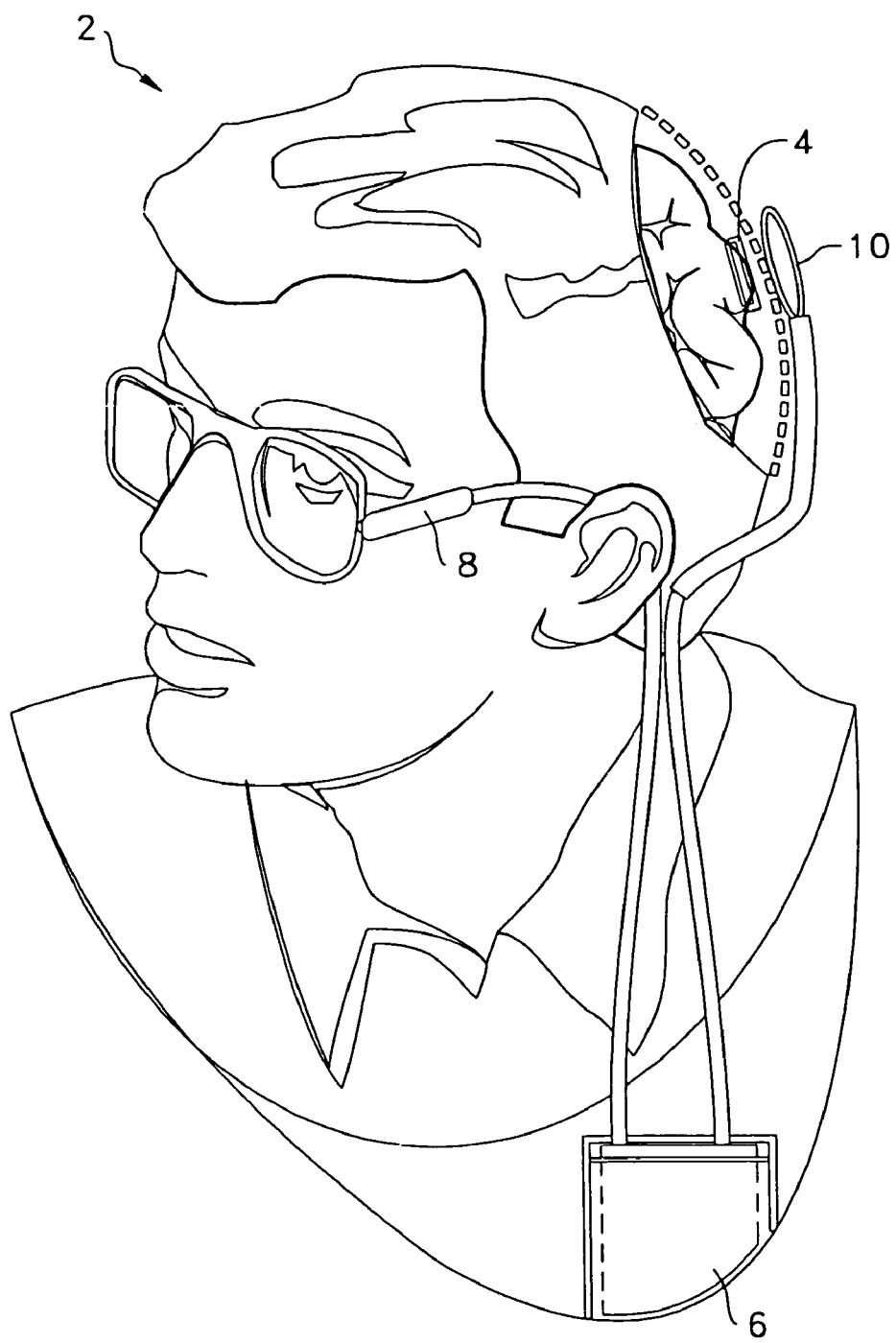
FIG. 21 is a schematic diagram illustrating a body implant artificial vision system worn by a user according to the present invention.

Referring to FIG. 21, there is shown a body implant system worn by a user 2 according to the present invention, in the context where the user 2 is a blind person and the system is used to provide artificial vision to the user 2. It should be understood that this context exemplifies a typical use of the implant system according to the present invention, and should not be taken in a limitative or restrictive sense, as the implant system may be used in many other contexts, for example for monitoring purposes, and especially for measuring parameters around an electrode-neuronal tissues interface.

The body implant system includes two main parts: an implant 4 positioned on the visual cortex of the user 2, and an external unit 6 that can be inserted in a pocket and which acquires real life scenes, processes the image information and communicates with the implant 4 to provide energy for powering the implant 4 and to control it in order to stimulate the visual cortex of the user 2 through an electrode array used to generate phosphenes in the visual field corresponding to a transposition of the real life scenes. The real life scenes can be acquired through a camera 8 (e.g. a CMOS image sensor) mounted on an earpiece of an eyeglass, while the implant energy and control signals can be transmitted through an inductive link using an antenna 10 positioned behind the head of the user 2.

Referring to FIGS. 1–6, there are shown two embodiments of the body implant assembly according to the present invention. These embodiments feature integration of most of the electronic components of the implant in a single full custom mixed-signal chip 12, thereby reducing power consumption and size of the circuit. Furthermore, a special interconnection circuit is provided for interconnection of the chip 12 with a high resolution electrode array 14 having multiple adjacent electrodes 16, e.g. a 25×26 array =650 electrodes made of biocompatible materials, having an average height of approx. 1, 5 mm, spaced by approx. 400 µm from one another and extending over a very small area, e.g. 1 cm². The resulting implant assembly is thus highly miniaturized compared to prior art implants, and the interconnection circuit provides individual connections to every electrode 16. The electrode array 14 can be made of several smaller electrode arrays assembled together (not shown), instead of a larger single array if desired.

Figure 2:
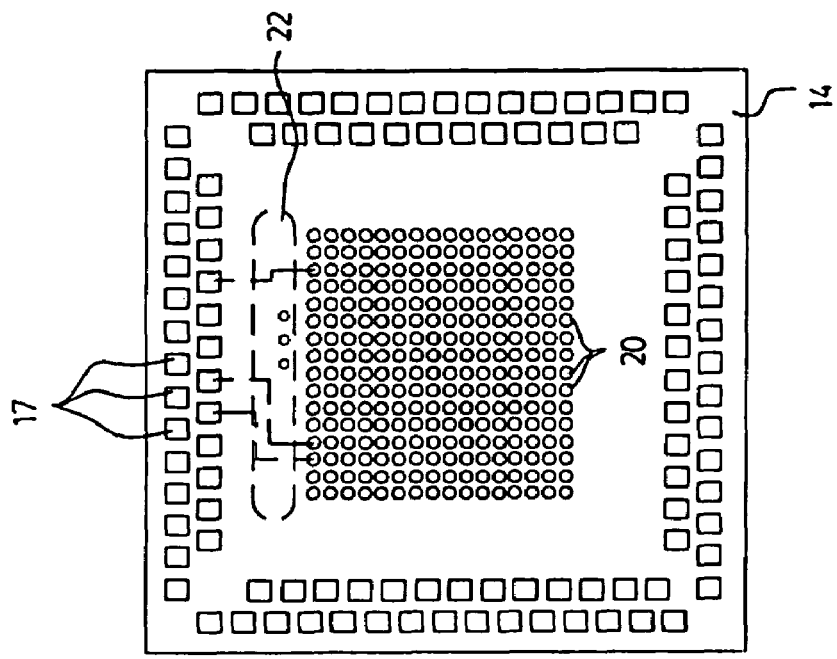
Figure 1:
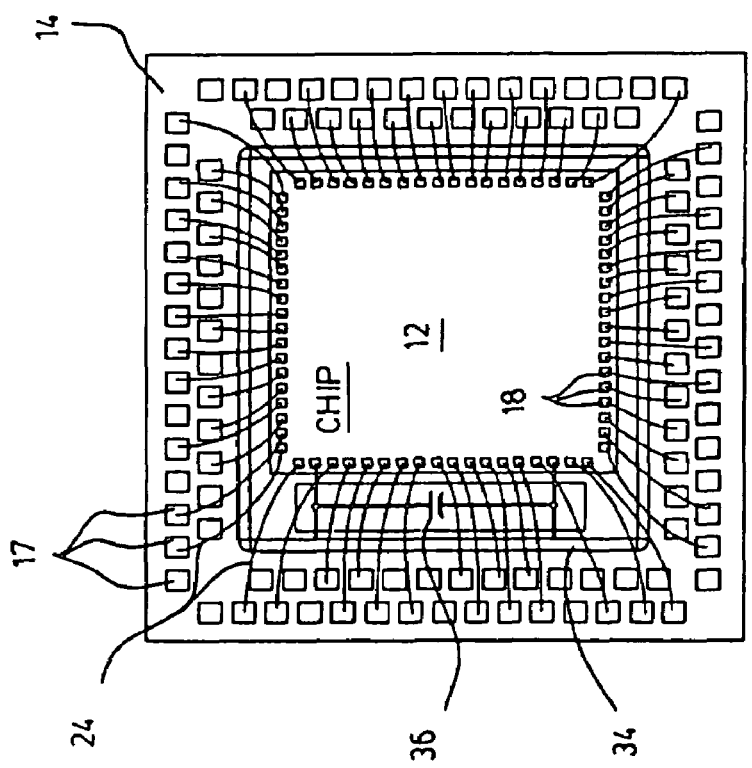

Referring to FIGS. 1–3, the chip 12 is embedded on a side of a very thin substrate support 14 having contacts 17 lying around the chip 12, at a given distance therefrom. These contacts 17 are respectively connected to the pads 18 of the chip 12 for example by a wire bond 24. The other side of the substrate support 14 is provided with an array of adjacent contacts 20 aligned with and connected to the electrodes 16 respectively. The connection of the contacts 20 with the electrodes 16 can be achieved by cold welding or any other suitable technique. The contacts 17 and 20 on both sides of the substrate support 14 are interconnected respectively together by an interconnection circuit 22 across the substrate support. Depending on the number of links to achieve, the interconnection circuit 22 may be formed of layers made in the substrate support 14 and stacked between the sides thereof. To reduce the space taken by the contacts 17, they may be distributed in an alternate shifted pattern over two or more adjacent sets of rows surrounding the chip 12. The body implant assembly resulting from this embodiment is thus very thin for a reasonable cross section. An antenna 34 extends on the substrate support 14 around the chip 12 for communication with the external unit 6. The antenna 34 is connected to pads 18 of the chip 12 assigned for this purpose. A capacitor 36 is coupled to the antenna 34 for proper operation. Other suitable antenna configurations may be used.

Figure 5:
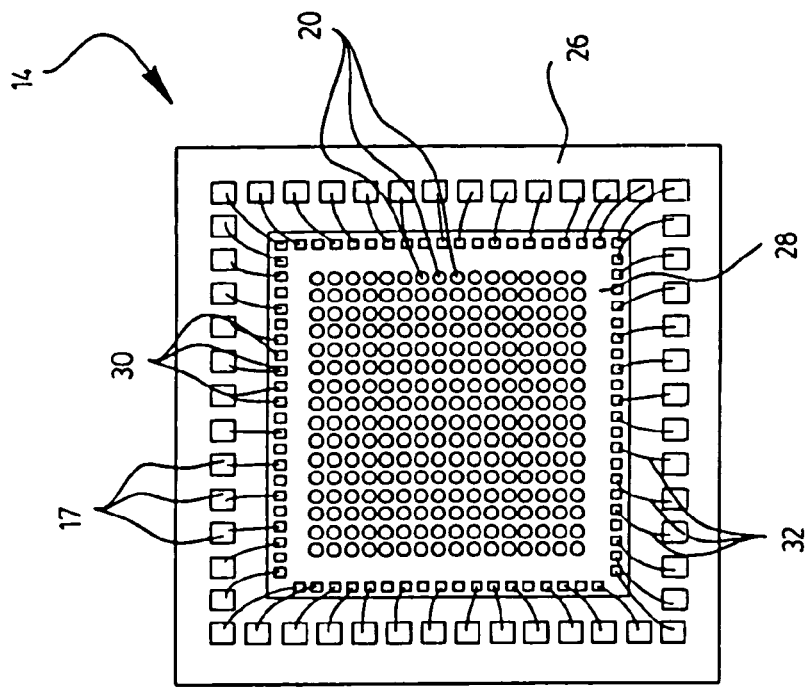
FIGS. 4, 5 and 6 are, respectively; schematic views of front and rear sides of a substrate support of a body implant assembly and an exploded view thereof with an electrode array according to another embodiment of the present invention.
Figure 4:
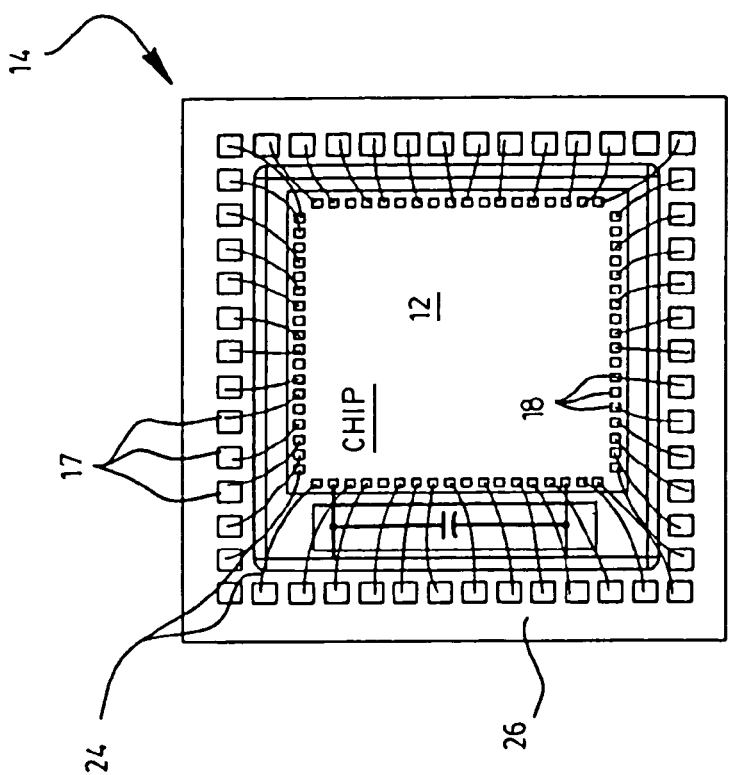
Figure 6:
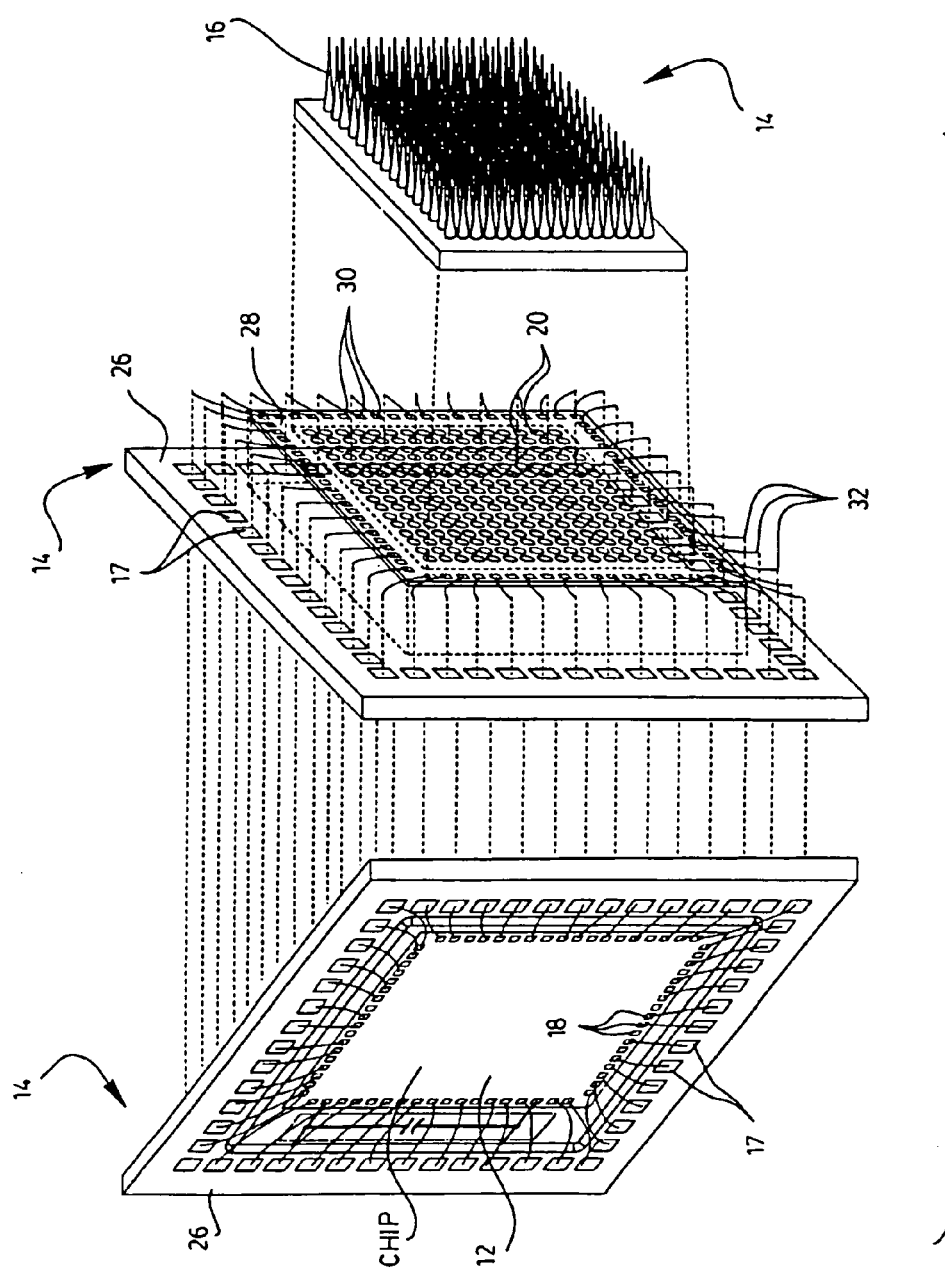

Referring to FIGS. 4–6, the substrate support 14 may be formed of a front relatively flat portion 26 having however a smaller cross section than the substrate support 14 in the former embodiment, and a smaller rear portion 28 projecting behind the front portion and receiving the electrode array 14. As in the former case, the contacts 17 on the foremost face of the front portion 26 are connected respectively to the pads 18 of the chip 12. The contacts 17 however also project through and appear behind the front portion 26. The interconnection circuit in this case has a series of peripheral contacts 30 surrounding the array of adjacent contacts 20 on the rearmost face of the rear portion 28. The peripheral contacts 30 and the contacts 17 appearing behind the front portion 26 are respectively connected together by a wire bond 32. Circuit layers of suitable designs made in the rear portion 28 and stacked between the rearmost and foremost face thereof interconnect the peripheral contacts 30 with the array of adjacent contacts 20 respectively. The body implant assembly resulting from this embodiment is thus thicker than in the former embodiment, but as a smaller cross-section.

In both of the above embodiments, the body implant assembly can be made from a silicon die containing all the electronic circuitry necessary to receive command words, detect and correct transmission errors, decode the command words and control the stimulation process accordingly.

Figure 7:
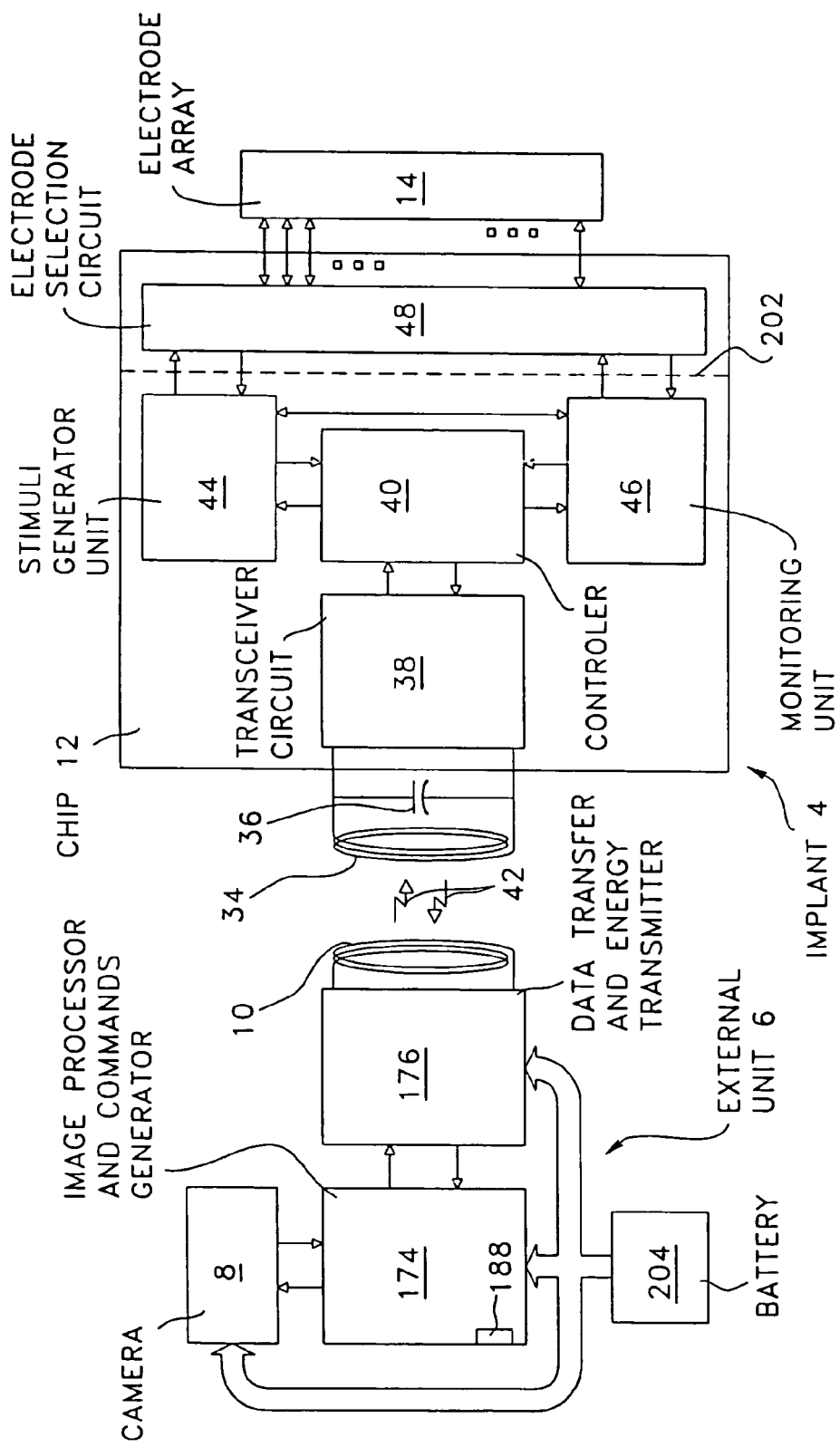
FIG. 7 is a schematic diagram of a body implant system according to an embodiment of the present invention.

Referring to FIG. 7, the full custom mixed-signal chip 12 preferably integrates a FM bi-directional data transfer & energy receiver 38, a controller 40, a stimuli generator unit 44, an optional but generally desirable monitoring unit 46, and depending on the chosen design, an electrode selection circuit 48 or not as it can also be provided as a separate circuit from the chip 12 as depicted by the dotted lines 202, then forming another full custom chip.

The receiver 36 recovers high frequency AC signal from the implant control signal emitted by the external unit 6, and transforms it to a DC voltage. This DC voltage is used to power up the whole implant. The receiver 38 recovers also clock and data from the same implant control signal emitted by the external unit 6, and transmits it to the internal controller 40. The receiver 38 gets feedback data from the internal controller 40 and transmits it to the user through the inductive link depicted by arrows 42. The receiver 38 thus acts as a transceiver. Although the feedback function is likely to be indispensable in most applications, it can nevertheless be omitted if it is really useless for a specific application.

The controller 40 decodes the commands generated by the external unit 6 in order to produce all control signals to the stimuli generator unit 44 and the monitoring unit 46.

Figure 8:
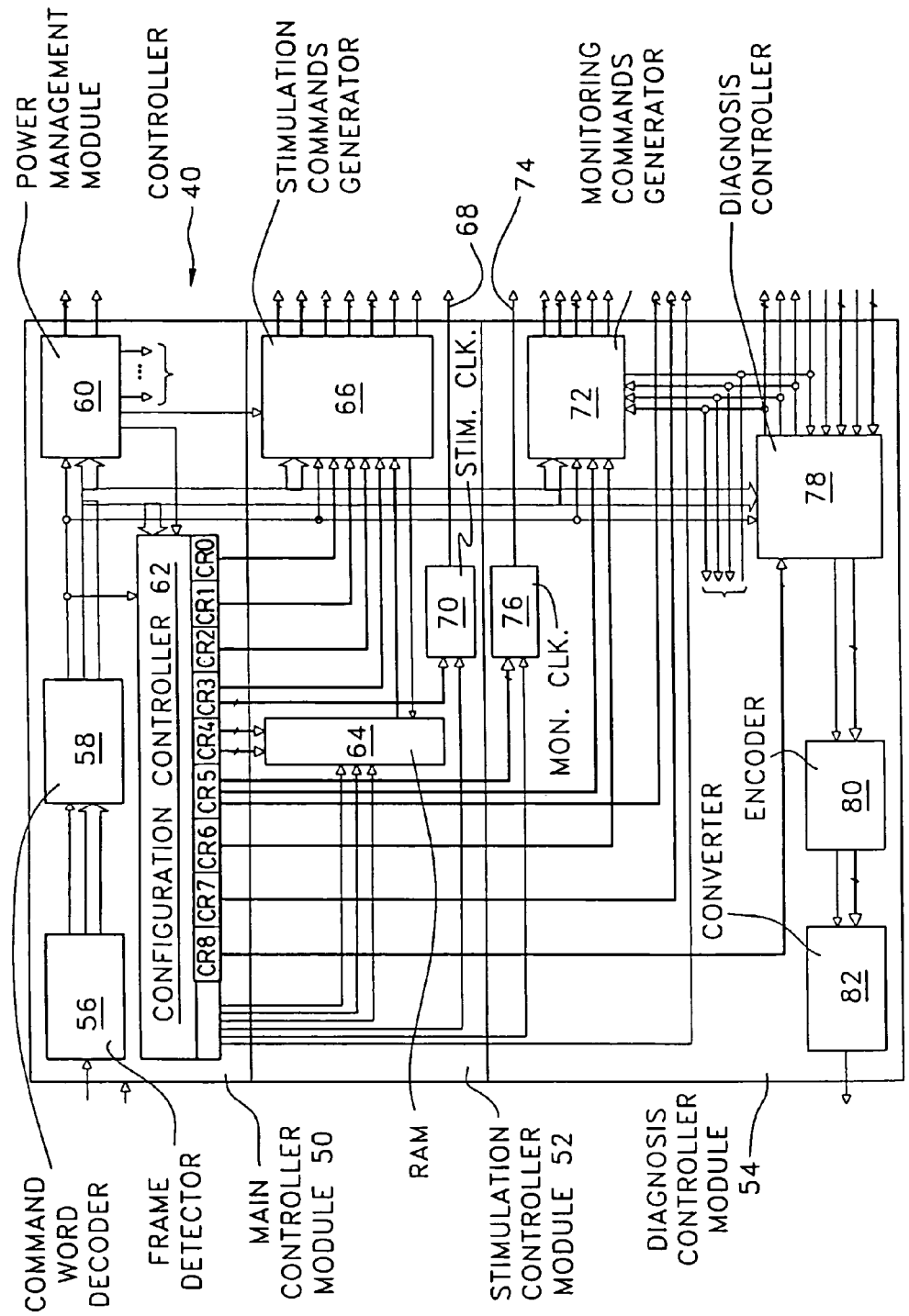
FIGS. 8, 9, 10 and 11 are schematic diagrams of the internal controller, the stimuli generation circuit, the monitoring circuit and the electrode selection circuit of a body implant according to the present invention.

Referring to FIG. 8, the controller 40 may be embodied by a circuitry mainly containing 12 units, which are grouped into 3 main sections: a main controller module 50, a stimulation controller module 52, and a diagnosis controller module 54. The main controller module 50 detects data frames and corrects communication errors, if present, in order to build the command words used by the other modules in the controller 40. This can be achieved through a serial/parallel converter & frame detector 56 and an error correction & command word decoder 58.

A power management module 60 (PMM) can be provided to turn other modules, units, or stimulation channels on or off individually to keep power consumption to a minimum at any given time. Only the PMM 60 itself and the two previous modules 56, 58, necessary for command reception, are not susceptible to being turned off. Turning a module off means lowering its power consumption down to zero, but does not imply a real shut down of the unit, keeping programmed parameters valid where volatile memory is used. For sake of clarity, only few of the many control lines to the controller's internal modules are presented in FIG. 8.

A configuration controller 62 preferably keeps every communication, stimulation, and diagnosis parameter programmed by the user by means of registers CR0–CR8, and makes them available for other modules or units. A Power-On-Reset function controlled by the main controller 50 can be implemented.

A proper knowledge of the communication protocol for the implant as set forth hereinafter might be important for understanding the following part.

The stimulation controller module 52 has a Random Access Memory 64 (RAM) intended to keep a stimulation channel/site address sequence programmed by the external unit 6 during the configuration process.

A stimulation commands generator 66 (SCG) decodes the stimulation instructions and sends the required control signals to the stimuli generator unit 44 (as shown in FIG. 7), according to programmed shared stimulation parameters, if applicable.

A clock signal 68 whose frequency depends on a specific programmed parameter SCTB stored in the register CR3 is used for stimulation by the stimuli generator unit 44 and is generated by a stimulation clock module 70.

The diagnosis controller module 54 has a monitoring commands generator 72 (MCG) which decodes the diagnosis instructions related to the analog monitoring of the stimulation system and electrode/tissue condition, and sends the required control signals to the monitoring unit 46 (as shown in FIG. 7), according to the programmed options/parameters.

A clock signal 74 whose frequency depends on a specific programmed parameter MCTB stored in the register CR5 is used for monitoring purposes by the monitoring unit 46 and is generated by a monitoring clock module 76.

A diagnosis controller 78 (DC) transmits test vectors sent by the external unit 6 upon request to any module and units, and receives test results thereof, both from digital tests and from analog monitoring performed by the monitoring commands generator 72. The DC 78 also sends the results back to the external unit 6, via parity insertion & return word encoder and parallel/serial converter modules 80, 82. For sake of clarity, only a few of the many control lines to the controller's internal modules are presented in this FIG. 8.

Figure 9:
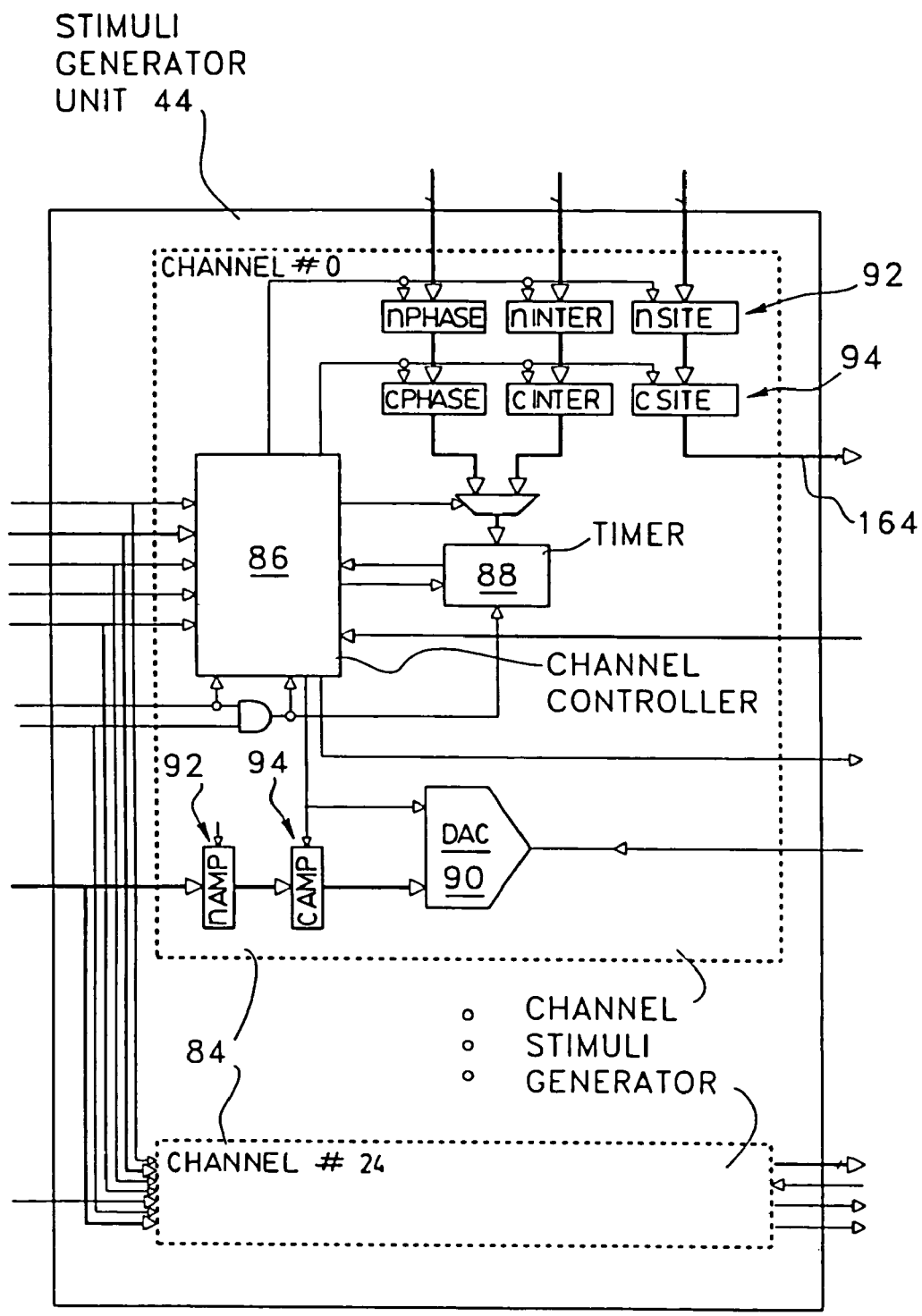

Referring to FIG. 9, the stimuli generator unit 44 may be embodied by a circuitry composed of 25 individual and independent channel stimuli generators 84 (CSG). Each of the CSG 84 has a channel controller 86 (CC), a timer module 88 and a current digital to analog converter 90 (DAC).

Two sets of registers 92, 94 allow to load the next stimulation parameters while the current ones are used, thereby eliminating delays between two successive stimulations. Not shown are the diagnosis signals to/from the controller's diagnosis controller module 78 (see FIG. 8) for testability and the power management control signals from the power management module 60.

Figure 10:
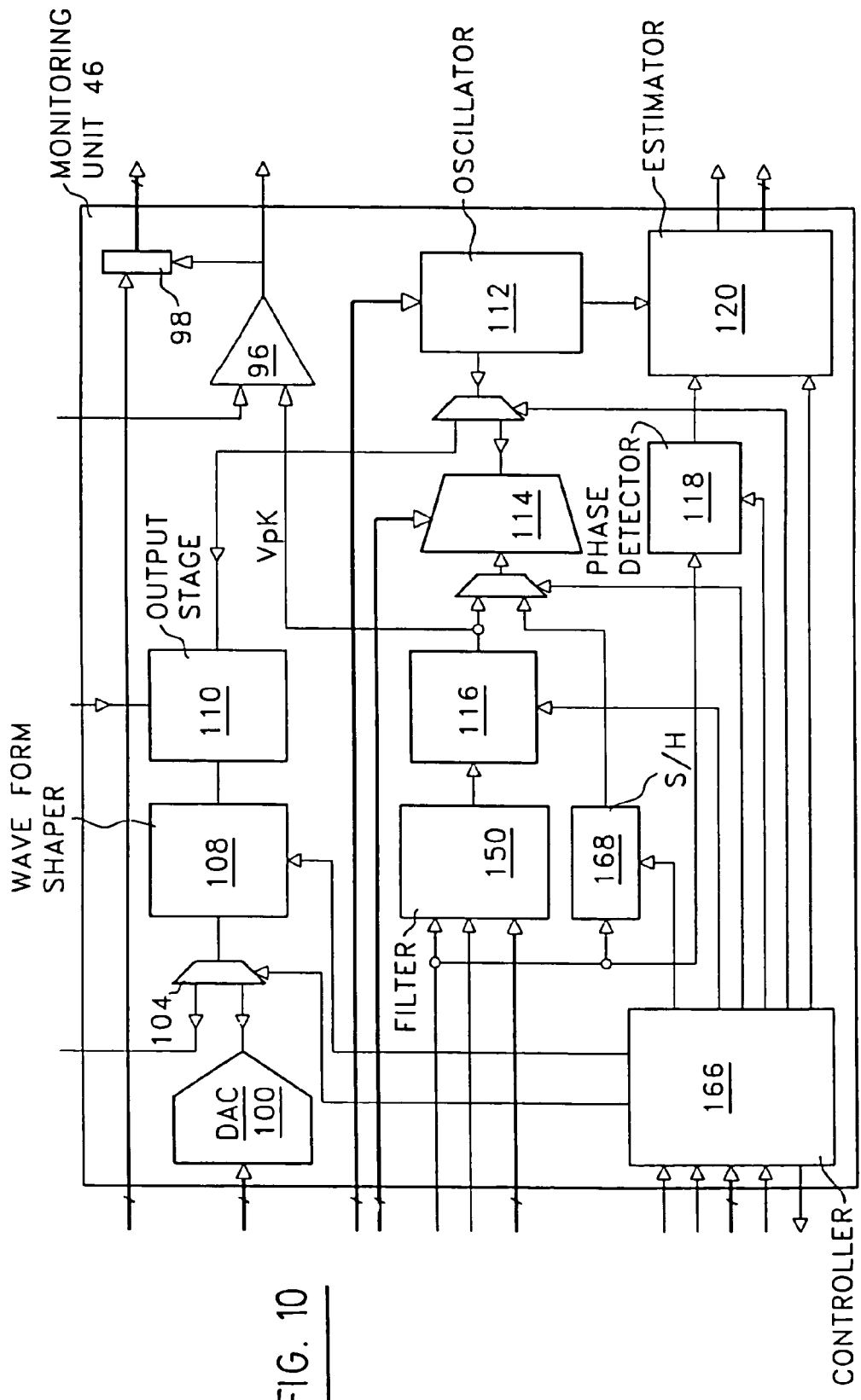

Referring to FIG. 10, the monitoring unit 46 may be embodied by a circuitry having the necessary sources and measurement modules to perform real/time continuous stimulation supervision and detailed voltage/current/complex impedance measurement for detailed diagnosis.

During normal stimulation, continuous monitoring can be performed by constantly comparing the peak voltage Vpk across any monitored stimulation site Prb0, Prb1 to a maximum reference voltage VRef, through comparator 96. If the monitored voltage exceeds the reference, the channel overflow signal ChanOF is activated and the channel on which the problem arose is stored in a register 98 DefChan. The reference signal VRef is set by the maximum allowed current and impedance between any stimulation site monitored by the DAC 100 and in accordance with the parameter CalRes stored in the register CR6 of the configuration controller 62 shown in FIG. 8 and sent to the calibration channel decoder 102 shown in FIG. 11.

Many options are available for detailed diagnosis. The source may be either internal, then using the DAC 100 for this purpose, or external and then using any of the channel's DAC 90 shown in FIG. 9, as selected by the MonSrc signal produced by the demultiplexer 104 and operating the transistor arrangements 106 shown in FIG. 11. A waveform shaper 108 may be used to provide an unaltered square wave or a sine shaped wave for testing purposes. An output stage 110 provides the electrode array 14 with a stimulation current MonStim transmitted to the transistor arrangements 106 and provides the monitoring circuit 46 with an accurate voltage dependent copy of the stimulation current, which may be measured via a current controlled oscillator 112, whose range can be modified according to the input signal level OscRng derived from the parameter OCR stored in the register CR7 of the configuration controller 62 shown in FIG. 5. Any sampled voltage across the monitored site can be measured with the same oscillator 112 through a transconductance amplifier 114 with variable gain for various input voltage ranges as set by the signal GmRng. The peak magnitude of the voltage across the monitored site can be measured by means of a peak detector 116. The phase between the stimulation current and the monitored voltage can be measured through a phase detector 118 and a frequency and phase estimator 120 for complex impedance measurements. A monitoring unit controller 166 controls most of the components of the monitoring unit 46 in accordance with the various control signals produced by the monitoring commands generator 72 (see FIG. 8). A sample and hold circuit 168 is provided for the transconductance measurement.

Not shown are the diagnosis signals to/from the controller's diagnosis controller 78 (see FIG. 8) for testability and the power management control signals from the power management module 60.

It should be noted that in the case where the implant 4 is intended to be used solely for monitoring purposes, then all the circuits of the implant 4 with functions only related to the generation of stimulation signals can be removed from the implant 4 inasmuch as no stimulation signals are required. Such is the case when the implant 4 is used for example to monitor certain body organs producing measurable electric signals to be monitored. For example, the DACs 90 and 100 (see FIG. 10), and the stimulation commands generator 66 (see FIG. 8) can be omitted in such a case.

Figure 11:
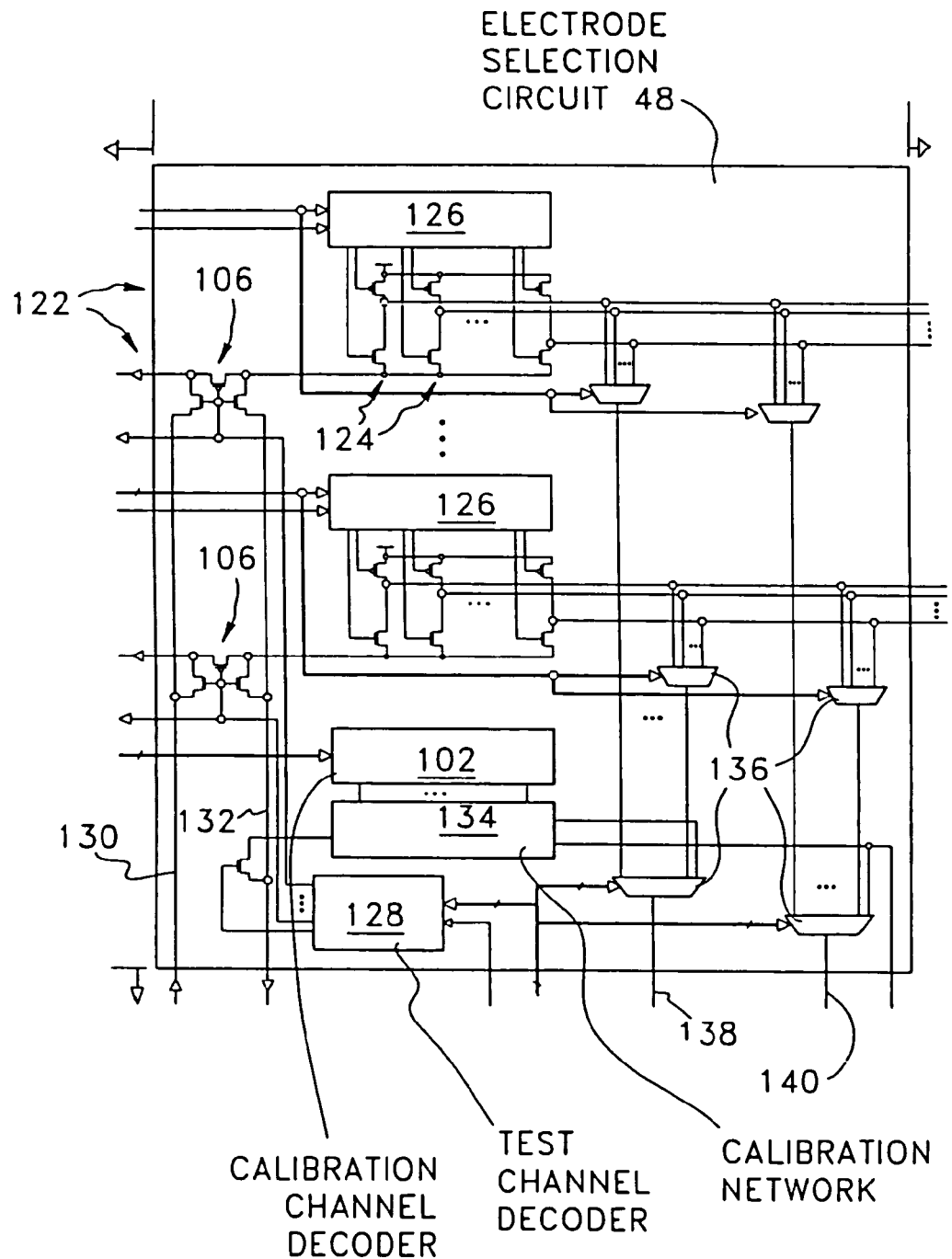

Referring to FIG. 11, the electrode selection circuit 48 can be embodied by a multiplexor/demultiplexor circuitry comprising 25 selection channels 122 provided with channel decoders 126 for activating up to 25 sites simultaneously. Each site can be activated in both directions by means of switch arrangements 124, depending on the sign bit (signal Sign #x) for every channel.

A test channel decoder 128 selects which channel has to be monitored. When a specific channel is monitored, the current from the corresponding channel stimuli generator 84 in the stimuli generator unit 44 is deviated to the monitoring unit 46 through the MonSrc line 130 and the stimulation current comes from that latter unit through the MonStim line 132. The channel stimuli generator 84 is notified that its channel is being monitored with the MonChan#x signal transmitted to corresponding the channel controller 86.

The electrode selection circuit 48 may be provided with a calibration channel circuit formed of the channel decoder 102 and a calibration network 134 and used by the analog monitoring unit 46. The calibration channel decoder 102 selects an appropriate known resistive element value. This is also used in the continuous monitoring process, generating the appropriate reference limit voltage VRef.

Sets of analog multiplexers 136 provide the monitoring unit 46 with the voltage across any pair of electrodes through the Prb0 and Prb1 lines 138, 140.

Figure 12:
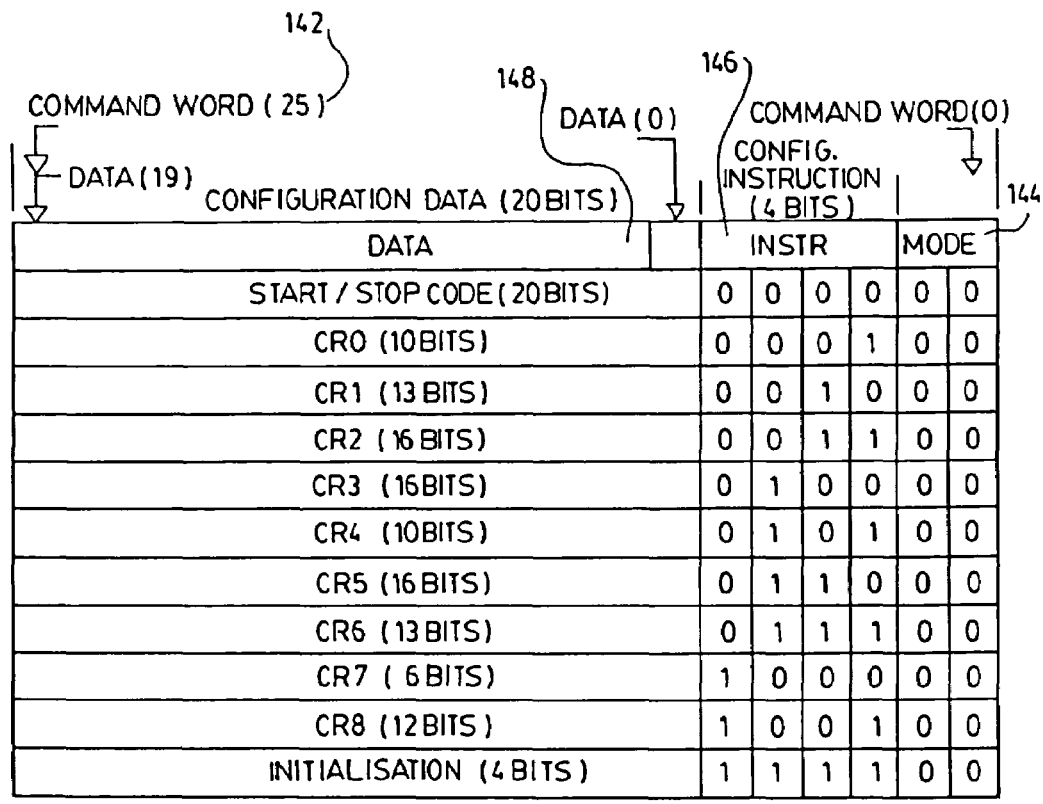
FIG. 12 is a schematic diagram illustrating a possible format of a communication protocol for a body implant according to the present invention.

Referring to FIG. 12, there is shown a possible format of a communication protocol for the body implant according to the present invention. In the illustrated case, the command words 142 are 26 bits long or less and are composed of three parts, the mode identification bits 144, the instruction 146 and the data 148. Note that each instruction 146 can contain one or several parts, depending on the selected mode.

A session usually starts with a configuration process. Then the stimulation period can start, according to the programmed configuration parameters 148 transmitted by the external unit 6. If a problem arises, the diagnosis mode allows a monitoring of both analog and digital components of the system. Finally, at any time, the power management mode enables the external unit 6 to turn on or off any component for reduced power consumption.

The configuration mode set by the command word <1, 0>==00 allows to define several variable parameters related to stimulation or monitoring.

The first five configuration registers CR0 to CR4 of the configuration controller 62 (see FIG. 8) define the communication protocol during stimulation. The next four registers CR5 to CR8 define many diagnosis parameters, the first three being dedicated to the analog monitoring and the last one relating to digital diagnosis of the system.

Figure 13:
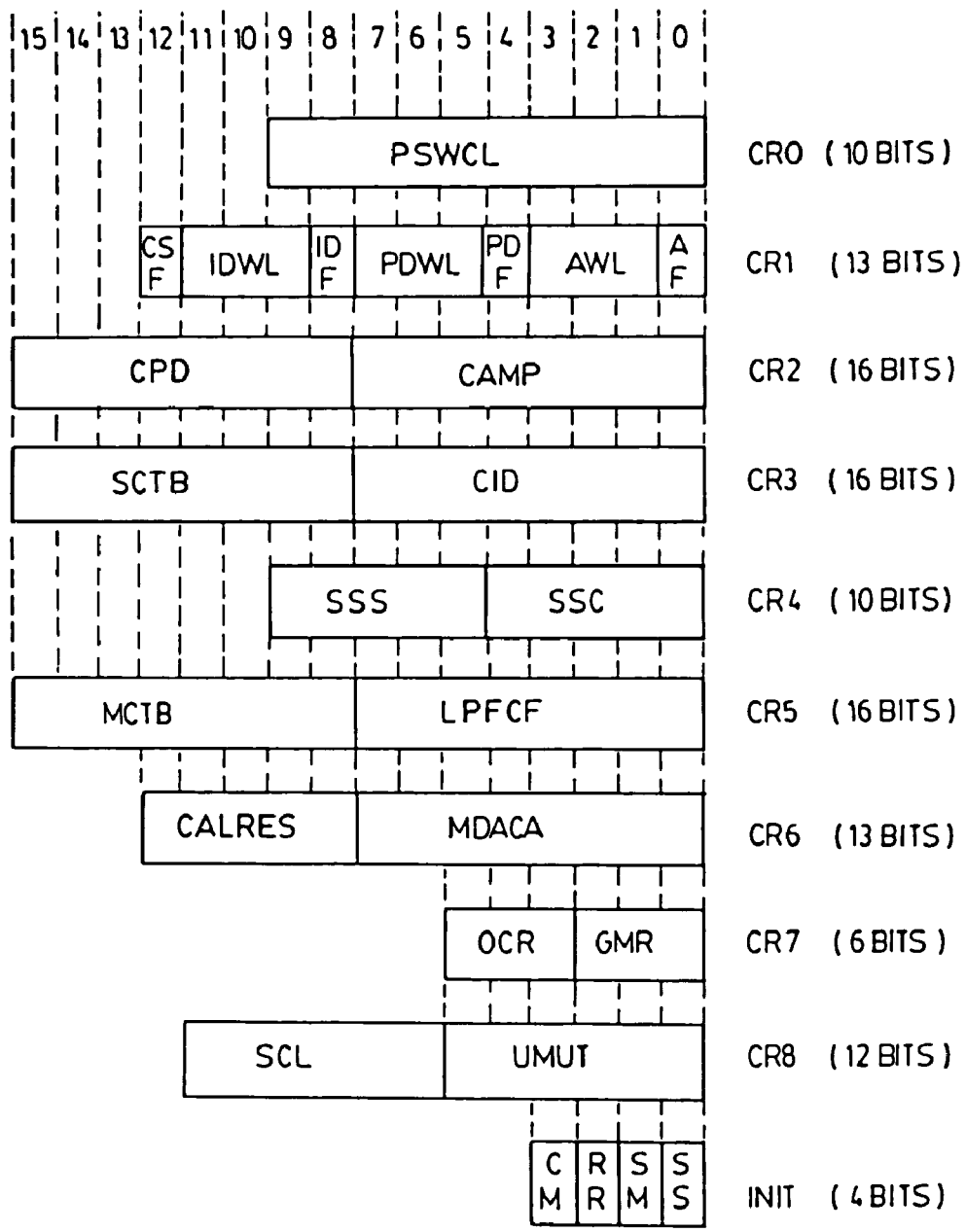
FIG. 13 is a schematic diagram illustrating possible definitions of parameters in the registers of an internal controller of a body implant according to the present invention.

Referring to FIG. 13, the definition of the parameters in the registers CR0–CR8 is as follows. The Partial Stimulation Word Chain Length (PSWCL) parameter defines the number of sequential stimulation words that are sent without interruption. The Amplitude Flag (AF) parameter defines whether the stimulation current amplitude is specific or common for every site. The Amplitude Word Length (AWL) parameter defines the number of bits specifying the amplitude of the stimulation current. The Pulse Duration Flag (PDF) parameter defines if the stimulation current pulse duration is specific or common for every site. The Pulse Duration Word Length (PDWL) parameter defines the number of bits specifying the pulse duration of the stimulation current. The Interphase Duration Flag (IDF) parameter defines if the delay between the two phases of the stimulation current is specific or common for every site. The Interphase Duration Word Length (IDWL) parameter defines the number of bits specifying the delay between the two phases of the stimulation current. The Common Amplitude (CAMP) parameter defines the amplitude of the stimulation current if this parameter is common for every site. The Common Pulse Duration (CPD) parameter defines the pulse duration of the stimulation current if this parameter is common for every site. The Common Interphase Duration (CID) parameter defines the delay between the two phases of the stimulation current if this parameter is common for every site. The Stimulation Clock Time Base (SCTB) parameter defines the frequency of the stimulation clock 70 shown in FIG. 8. The Stimulation Sequence Channel (SSC) and the Stimulation Sequence Site (SSS) parameters are used to fill the Stimulation Sequence RAM 64 shown in FIG. 8. The Low Pass Filter Cut-off Frequency (LPFCF) parameter defines the cut-off frequency of the Gm-C low-pass filter 150 shown in FIG. 10 in the monitoring unit 46. The Monitoring Clock Time Base (MCTB) parameter defines the frequency of the monitoring clock 76 in the controller 40 (see FIG. 8). The Monitoring DAC Amplitude (MDACA) parameter defines the amplitude of the output current of the DAC 90 (FIG. 9) for continuous monitoring. The Calibration Resistor (CALRES) parameter defines the reference equivalent resistor in the calibration network 134 for continuous monitoring (see FIG. 11). The Transconductance Range (GMR) parameter defines the gain of the transconductance amplifier 114 (see FIG. 10). The Oscillator Current Range (OCR) parameter defines the input current range of the current controlled oscillator 112 (see FIG. 10). The Unit/Module Under Test (UMUT) parameter defines the unit or module under test for digital diagnosis. The Scan Chain Length (SCL) parameter defines the number of bits of the scan chain in the unit or module under test. The Stimulation clock Sync (SS) parameter synchronizes the stimulation clock 70 (FIG. 8). The Monitoring clock Sync (MS) parameter synchronizes the monitoring clock 76 (FIG. 8). The RAM Reset (RR) parameter resets the address pointer of the Stimulation Sequence RAM 64 (FIG. 8) to zero. The Continuous Monitoring (CM) parameter turns the continuous monitoring feature of the controller 40 (FIG. 7) on/off.

Figure 14:
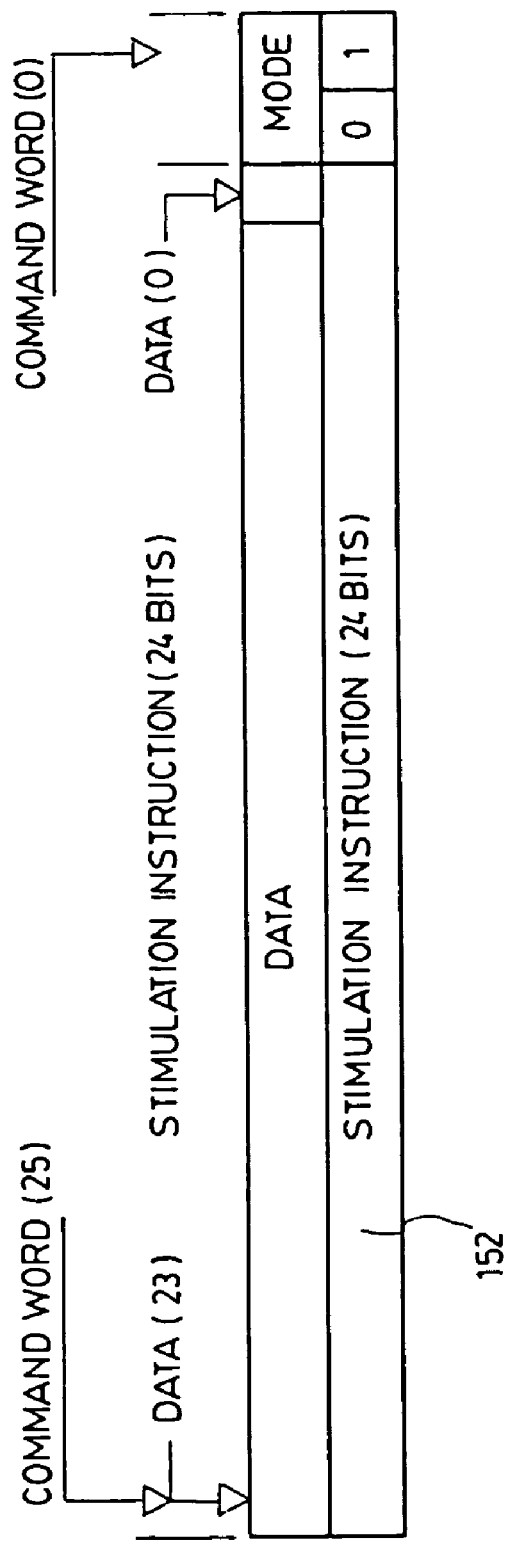
FIG. 14 is a schematic diagram illustrating a stimulation mode command format for a body implant according to the present invention.

Referring to FIG. 14, in the stimulation mode set by the command word <1, 0>==01, the instruction 152 depends directly on the stimulation communication protocol defined in the configuration. The instruction 152 is sent as a chain of a certain number (PSWCL) of stimulation words, each containing 1 to 34 bits, depending on the common parameters. If the chain is longer than 24 bits, it is divided into sequential stimulation instruction words of 24 bits or less for the last word.

Figure 15:
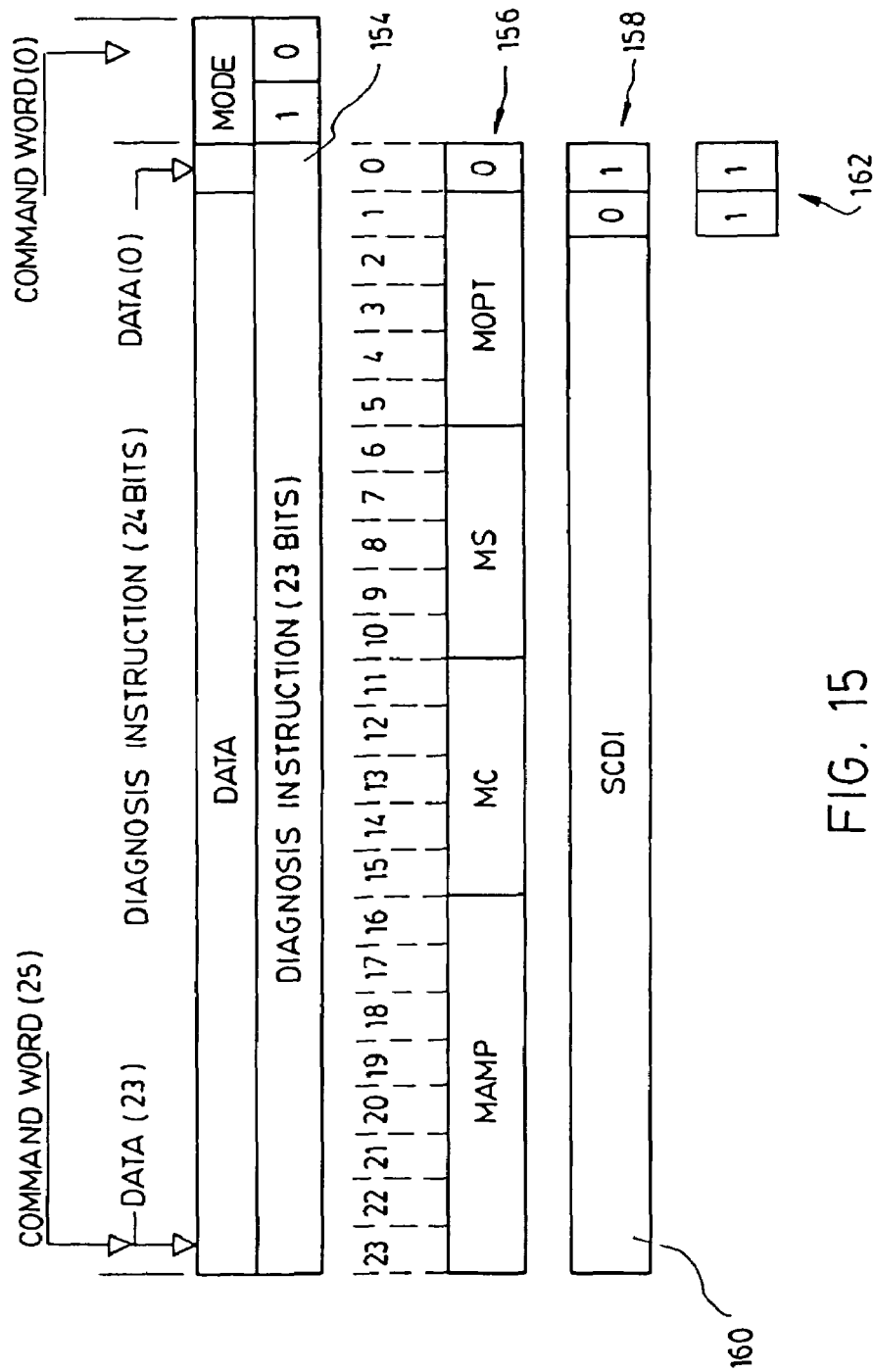
FIG. 15 is a schematic diagram illustrating a diagnosis mode command format for a body implant according to the present invention.

Referring to FIG. 15, the diagnosis mode set by the command word <1, 0>==10 allows detailed and various analyses of the condition of the system, on both the digital and analog sides. When the first bit of the diagnosis instruction word 154 is set in a low state 156, the following data is used to determine the information required for analog monitoring. The instruction is then composed of: a Monitored Site (MS) parameter, a Monitored Channel (MC) parameter, a Monitoring current Amplitude (MAMP) parameter, and a Monitoring Options (MOPT) parameter. The MOPT parameter specifies what the stimulation source is, what the stimulation waveform is, if the measured value is a current, if the measured value is a voltage, and if the measured value is the phase between current and voltage.

When the first bit of the diagnosis instruction word 154 is set in a high state 158, the diagnosis concerns the digital system. To input a test vector, the next bit is set to a low state and the vector 160 itself follows. If the length of the test vector is longer than 22 bits as defined by the SCL parameter in the configuration mode, the 23rd and next bits are sent in a subsequent similar diagnosis instruction word.

To read the data in a particular module of the system, both the first and second bit of the diagnosis instruction word are set in a high state 162. The controller will then send the test result back to the external unit 6.

Figure 16:
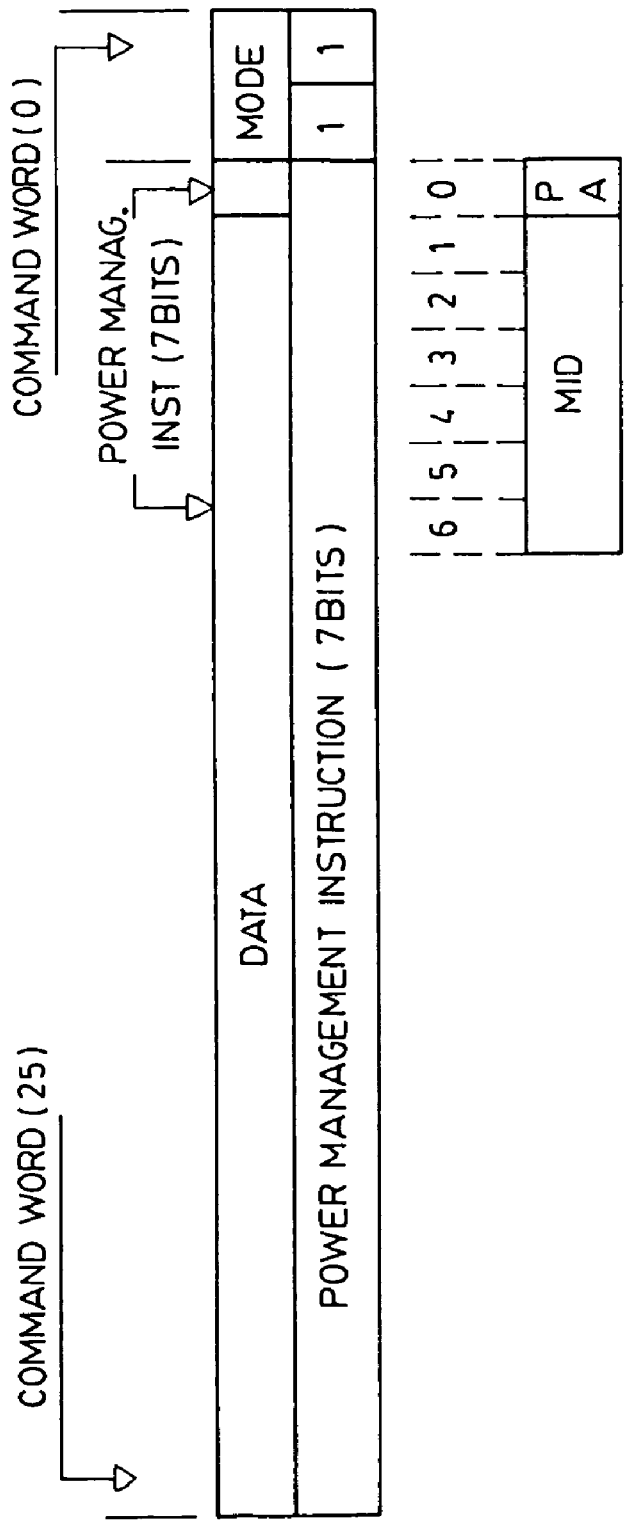
FIG. 16 is a schematic diagram illustrating a power management mode command format for a body implant according to the present invention.

Referring to FIG. 16, the power management mode set by the command word <1, 0>==11 allows to turn any component of the system on and off. The two parameters supplied in this mode are the power management action (PA), which defines if the unit/module has to be turned on/off, and the unit/module identification (MID) that defines which unit/module the power management action has to be applied to.

As mentioned hereinabove, the stimulation biphasic current pulses used to generate a phosphene can be described by three parameters, which are the amplitude, the phase duration and the inter-phase duration of the pulses. Each one of theses parameters, as well as the pulse frequency, influences the phosphenes visual appearance. It would require a high data transmission rate to send in real time all the stimulation parameters as well as the addresses of the corresponding stimulation sites from the external unit 6 to the implant 4. In order to reduce this rate, the needed stimulation data can be transferred as follows. First, each of the parameters is, beforehand, defined to be common or specific. A common parameter is shared by all the stimulation sites and has to be loaded only once at the beginning. However, the specific parameters have to be updated at each activation site. As an example, the phase and inter-phase durations can be common, and the amplitude can be specific. Using one or two common parameters allows a significant reduction in the transmission rate between the external unit 6 and the implant 4. The choice of which parameters are common or specific, as well as the number of bits necessary to specify each one of them can be set at any time in the configuration mode.

Secondly, instead of sending the stimulation site address with each parameter, the RAM 64 (FIG. 8) is used.

During the configuration phase of the implant 4, the external unit 6 fills the memory 64 with the scan sequence of each frame in an image that will be used by both devices (the implant 4 and the external unit 6). The stimulation parameters are then sent in the order specified in the memory 64.

This kind of transfer of the needed data makes the implant 4 highly configurable, allowing the external unit 6 to fully control the stimulation operations and allowing a higher frame (image) transmission rate, if needed.

Referring to FIG. 8, in operation, the stimulation commands generator 66 combines the common parameter data with each specific stimulation word to generate the proper stimulation control signals for the stimuli generator unit 44, indicating in particular the amplitude of the biphasic pulse (StimAmp), the phase duration of the pulse (PhaseDur), the interphase duration of the pulse (InterDur), the stimulation site address (StimSite), the stimulation channel number (StimChan).

Referring to FIG. 9, when a particular channel controller 86 receives the stimulation control signals, it loads the data into the set of temporary registers 92. Once the previous stimulation is completed, the data are transferred into the main registers 94 as a result of a control performed by the channel controller (Idnp and Idcp signals). The DAC 90 is responsive to the channel controller 86 (Stim signal) and generates a stimulation current having an amplitude depending on the StimAmp value. The stimulation operation begins using the site address bus 164 to select the proper site in the channel and the Stim signal to start and stop stimulation. The channel controller 86 uses the timer 88 based on the stimulation clock 70 (FIG. 8) to set the phase and interphase durations of the pulses.

Referring to FIG. 7, the external unit 6 has an image processor and command generator module 174 connected to the camera 8 for processing image data signals corresponding to a real life scene captured by the camera 8, in accordance with predetermined processing operations, and for generating implant compatible stimulation commands causing the implant 4 to produce the artificial image on the visual cortex corresponding to the real scene image. A transceiver module 176 preferably in the form of a FM bi-directional data transfer and energy transmitter is connected to the image processor and command generator module, for producing airwave-transmitted implant control signals carrying the stimulation commands, as depicted by the arrows 42. The external unit 6 is preferably powered by a battery 204.

Referring to FIGS. 7 and 17, the processing operations performed by the image processor and commands generator 174 on the real life scene 170 subjected to acquisition 178 by the camera 8 can be a digitalization of the image data signals to form a digital image 180, an image reduction of the digital image 180 into a scaled down image 182 having a same resolution as the electrode array 14, and an image enhancement of the scaled down image 14 to form an enhanced image 184 corresponding to the artificial image produced by the implant unit 4 and from which the stimulation commands 186 are generated.

The external unit 6 may be provided with a pattern generation interface (not shown) where the command words are formed from internal patterns instead of the image sensor 8. Such a feature would allow to quickly test recognizable patterns like a square, a circle or a cross for adjustment of the implant 4 to the user 2.

Once the image 182 has the proper resolution, basic image enhancement techniques are preferably applied. The purpose of the enhancement is to give to the image more balanced contrasts and luminosity. The applied technique can be a linear histogram equalization consisting of stretching the image histogram to cover the totality of the available pixel intensity spectrum. It is not necessary to calculate the whole histogram since only the minimum and maximum pixel intensities are useful. With those values, a look-up table can be built to transform, one by one, each pixel of the initial image.

Figure 18B:
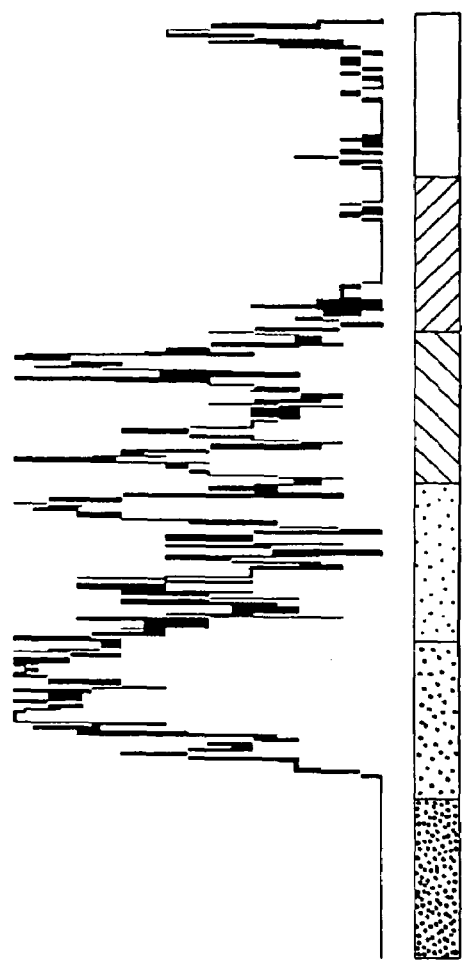
FIGS. 18A–B and 19A–B are schematic diagrams illustrating scaled down and enhanced images generated by an image processor and the corresponding histograms respectively, according to the present invention.
Figure 18A:
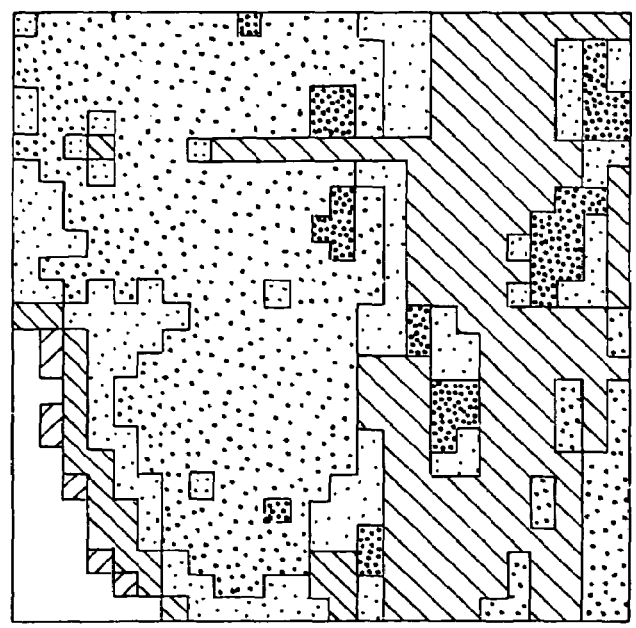
Figure 19B:
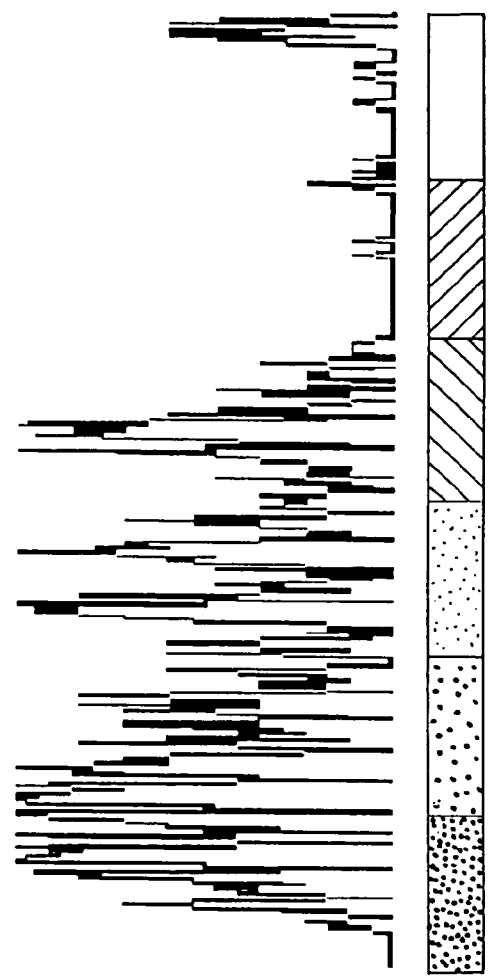
Figure 19A:
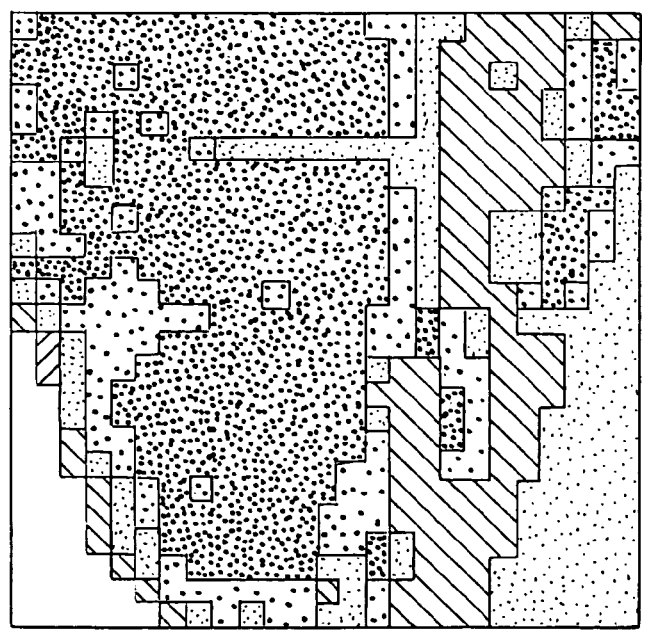

FIGS. 18A–B and 19A–B illustrate scaled-down and enhanced images generated by the image processor 174 (FIG. 7), and the corresponding histograms respectively. As it can be seen, the histogram shown in FIG. 19B, corresponding to the enhance image shown in FIG. 19A, covers a wider spectrum than the histogram shown in FIG. 18B for the image prior to enhancement as shown in FIG. 18A.

After the image enhancement, each pixel of the resulting image will represent a phosphene that should be created during the cortex stimulation. To create this phosphene, a command word must be created to specify every stimulation parameter, from waveform shape to phase delay. Since many of the parameters affect only the qualitative part of phosphene appearance and the effects of their modification is not currently thoroughly known, those parameters must be easily and quickly alterable. In addition, when stimulating biological cells with an electrical current, the stimulation of the same cells, or cells in the surrounding, cannot be repeated before a delay of few ms. This delay is called repolarization time. For this reason, serial scanning cannot be used for the stimulation of the cortex in order to create an image. Instead, a scan sequence must be selected in such a way that each sequential stimulation is not executed in an area where a stimulation occurred before the repolarization time is elapsed. The flexibility of the implant system according to the invention allows the use of any desired scanning sequence and the configuration of the implant 4 with the same sequence.

Figure 20:
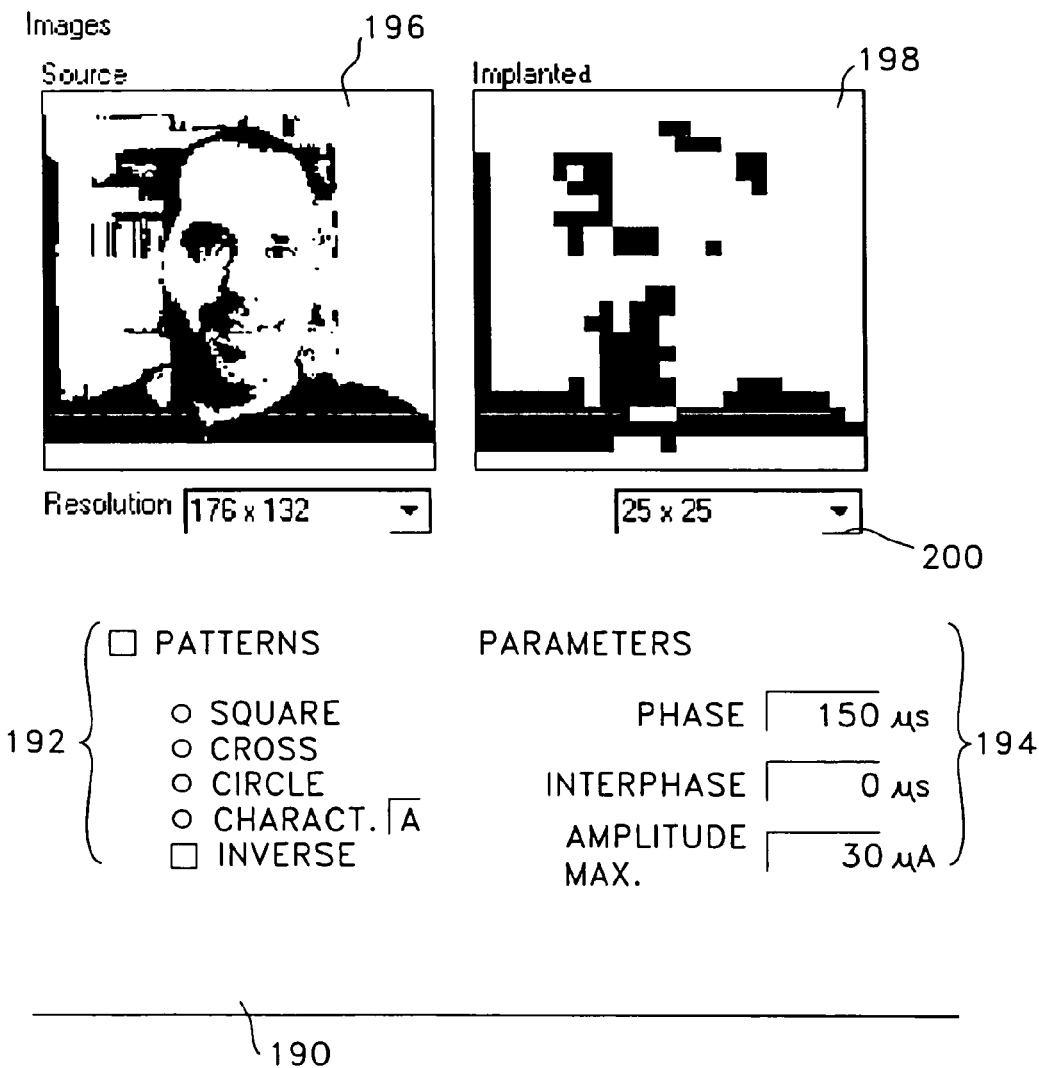
FIG. 20 is a schematic diagram illustrating a screen capture of an external unit user interface according to the present invention.

Referring to FIGS. 7 and 20, the external unit 6 may be provided with a communication port 188 for communication with a computer (not shown) for configuration and test purposes. For example, to test the system, easily recognizable shapes may be used to test the phosphene apparition parameters, as mentioned hereinabove. Those shapes can be generated by the external unit 6 in response to a test request issued by the computer, as inputted through a user interface 190. The user can select different patterns 192 and adjust the parameters 194 on the fly. For example, a square, a cross or a circle may be selected, each of which can be in a solid or outline form. Character generation can also be implemented to enable more complex shapes. For greater user control, those patterns may bypass the usual data pathway and directly generate the command words in the external unit 6.

The user interface 190 may display a source image 196 as captured by the camera 8 or from another source, and the corresponding image 198 reduced to the resolution of the electrode array 14, in its enhanced form. The reduced image resolution can be changed instantly within the drop down menu list 200.

Referring to FIG. 7, the camera 8 has preferably a variable resolution providing an electronic zoom function. Such a feature can be used to adapt the low resolution of the image transmitted to the implant 4 (e.g. 25×25) to the situation in which the user is. For example, the user may choose between a coarse view over a large field of vision or, conversely, a detailed view over a limited zone in order to discern the details of a point of interest or for reading purposes.

Instead of using a predetermined addressing process using the RAM 64 (see FIG. 8) as hereinabove described, which allows to reduce the pass-band of the transmitted data when the stimulation sequence and the pixel numbers are constant for each image, a specific addressing process can also be implemented to allow the stimulation sites to be chosen according to each image to be transmitted. Then, by setting a light intensity threshold under which the stimulation effect is considered to be negligible, certain pixels of the image will be simply disregarded by the external unit 6. As a result, power consumption can be thereby reduced while the image refresh rate is improved. Preferably, the threshold is adjustable in order to discriminate the pixels to be transmitted from those to be discarded. Other suitable addressing methods can also be implemented.

The implant system according to the invention can be equipped for example with an ultrasound sensor (not shown) having a large field of detection, preferably set as a function of the minimum zoom of the camera 8 or larger, providing information on the proximity of detected objects, which information affects the light intensity transmitted to the brain. Such a system would allow the user to move smoothly by following the dark or clear zones that he or she sees, without requiring visual recognition of the surrounding objects, which may be difficult to achieve at a low resolution (e.g. 25×25).

While embodiments of this invention have been illustrated in the accompanying drawings and described above, it will be evident to those skilled in the art that changes and modifications may be made therein without departing from the essence of this invention. All such modifications or variations are believed to be within the scope of the invention as defined by the claims appended hereto.

The invention claimed is:

1. A body implant assembly comprising:
   an electrode array having multiple adjacent electrodes directed towards respective stimulation sites;
   an antenna;
   a full custom mixed-signal chip including a transceiver circuit coupled to the antenna, an AC to DC transformation circuit coupled to the transceiver circuit and powering the full custom mixed-signal chip from energy contained in a control signal received by the transceiver circuit, a controller connected to the transceiver circuit and processing operation data contained in the control signal received by the transceiver circuit, and a stimuli generator circuit connected to the controller and generating stimulation signals in accordance with the operation data;
   an electrode selection circuit connected to the stimuli generator circuit and having selectable outputs for transmission of the stimulation signals to selected ones of the electrodes in accordance with the operation data; and
   a substrate support having a first side receiving the full custom mixed-signal chip, the antenna and the electrode selection circuit, and a second, opposite side receiving the electrode array, the first side having contacts lying around the full custom mixed-signal chip and connected to the outputs of the electrode selection circuit respectively, the second side having an array of adjacent contacts aligned with and connected to the electrodes respectively, the contacts on the first and second sides being respectively interconnected together by an interconnection circuit across the substrate support.

2. The body implant assembly according to claim 1, wherein the interconnection circuit comprises circuit layers made in the substrate support and stacked between the sides thereof, the circuit layers interconnecting the contacts on the first side with the contacts on the second side respectively.

3. The body implant assembly according to claim 1, wherein the contacts on the first side are distributed in an alternate shifted pattern over two adjacent sets of rows surrounding the full custom mixed-signal chip.

4. The body implant assembly according to claim 1, wherein: the substrate support has a substantially flat front portion embedding the full custom mixed-signal chip and the electrode selection circuit, and a smaller rear portion projecting behind the front portion and receiving the electrode array, the first and second sides of the substrate support being on foremost and rearmost faces of the front and rear portions respectively;

the contacts on the first side project through and appear behind the front portion around the rear portion; and the interconnection circuit comprises a series of peripheral contacts surrounding the array of adjacent contacts on the rearmost face of the rear portion, a wire bond interconnecting the peripheral contacts with the contacts appearing behind the front portion respectively, and circuit layers made in the rear portion and stacked between the rearmost face and a foremost face thereof, the circuit layers interconnecting the peripheral contacts with the array of adjacent contacts respectively.

5. The body implant assembly according to claim 1, wherein the full custom mixed-signal chip includes the electrode selection circuit.

6. The body implant assembly according to claim 1, wherein the antenna extend on the substrate support around the full custom mixed-signal chip.

7. The body implant assembly according to claim 1, wherein the full custom mixed-signal chip includes a monitoring circuit coupled between the electrode selection circuit and the controller, the monitoring circuit taking measurements of the stimulation signals in response to monitoring control signals issued by the controller depending on the operation data, and transmitting the measurements to the controller, the controller processing the measurements and transmitting test result signals to the transceiver circuit for emission out of the body implant depending on the operation data.

8. The body implant assembly according to claim 1, wherein the electrode array is made of biocompatible material, and has a 1 cm$^2$ cross-section, the electrodes comprising hundreds of needles distributed in rows and columns across the 1 cm$^2$ cross-section, and the substrate support has a thickness substantially less than 1 mm.

9. The body implant assembly according to claim 8, wherein the needles have an average height of 1, 5 mm and are spaced from one another by 400 μm.

10. A body implant comprising:
an electrode array having multiple adjacent electrodes directed towards respective stimulation sites;
an antenna;
a transceiver circuit coupled to the antenna;
an AC to DC voltage transformation circuit coupled to the transceiver circuit and providing implant power supply from energy contained in an implant control signal received by the transceiver circuit;
a controller connected to the transceiver circuit and processing operation data contained in the implant control signal received by the transceiver circuit;
a stimuli generator circuit connected to the controller and generating stimulation signals in accordance with the operation data; and
an electrode selection circuit connected between the stimuli generation circuit and the electrode array, the electrode selection circuit having selectable outputs for transmission of the stimulation signals to selected ones of the electrodes in accordance with the operation data;
the controller having a decoder circuit decoding the operation data contained in the implant control signal, a configuration controller storing common and specific stimulation parameters specified in the operation data and respectively addressed to all of the stimulation sites and specific ones of the stimulation sites, and a stimulation command controller transmitting stimulation control signals to the stimuli generator circuit in accordance with the common and specific stimulation parameters.

11. The body implant according to claim 10, wherein the controller further has a memory coupled between the configuration controller and the stimulation command controller, and storing a stimulation sequence specified in the operation data and representing an order of selection of the outputs of the electrode selection circuit for the stimulation signals respectively.

12. The body implant according to claim 10, wherein the common parameters comprise an amplitude of the stimulation signals, a duration of pulses in the stimulations signals, and a delay between two bipolar phases of the stimulation signals, the configuration controller storing an indication.

13. The body implant according to claim 10, wherein the decoder circuit comprises a frame detector detecting data frames contained in the implant control signal, and an error correction and command word decoder producing command words forming the operation data for the controller, the configuration controller and the stimulation command controller being connected to the error correction and command word decoder.

14. The body implant according to claim 10, wherein the transceiver circuit has an output producing a clock signal recovered from the implant control signal and transmitted to the controller as a timing base.

15. The body implant according to claim 10, wherein the controller has a power management module connected to the decoder circuit and to predetermined circuits of the body implant, for controllably turning said predetermined circuits on and off in accordance with the operation data.

16. A body implant comprising:
an electrode array having multiple adjacent electrodes directed towards respective stimulation sites;
an antenna;
a transceiver circuit coupled to the antenna;
an AC to DC voltage transformation circuit coupled to the transceiver circuit and providing implant power supply from energy contained in an implant control signal received by the transceiver circuit;
a controller connected to the transceiver circuit and processing operation data contained in the implant control signal received by the transceiver circuit;

a stimuli generator circuit connected to the controller and generating stimulation signals in accordance with the operation data;

an electrode selection circuit connected between the stimuli generation circuit and the electrode array, the electrode selection circuit having selectable outputs for transmission of the stimulation signals to selected ones of the electrodes in accordance with the operation data; and a monitoring unit coupled between the controller and the electrode selection circuit, and controllably taking signal measurements at selected ones of the stimulation sites in response to monitoring control signals and producing test result signals indicative of the signal measurements;

the controller having a decoder circuit decoding the operation data contained in the implant control signal, a monitoring command generator decoding diagnosis instructions contained in the operation data and transmitting the monitoring control signals to the monitoring unit in accordance with the diagnosis instructions, and a diagnosis controller receiving and processing the test result signals from the monitoring unit.

17. The body implant according to claim 16, wherein the monitoring unit has an internal signal source module generating test signals used as the stimulation signals depending on the monitoring control signals, a current and voltage measuring circuit measuring a stimulation current and a monitored voltage across a monitored one of the stimulation sites in response to a corresponding one of the stimulation signals, a peak detector measuring a peak magnitude of the voltage, and a phase detector measuring a phase between the stimulation current and the monitored voltage, the test result signals being derived from the stimulation current, the monitored voltage and the phase.

18. The body implant according to claim 16, wherein the diagnosis controller is connected to the transceiver circuit, the test result signals being transmitted from the diagnosis controller to the transceiver circuit for emission out of the body implant depending on the operation data.

19. The body implant according to claim 18, wherein the diagnosis controller has connections with predetermined circuits of the implant to transmit test vectors contained in the operation data thereto and to receive resulting test result signals thereof.

20. A body implant comprising:
an electrode array having multiple adjacent electrodes directed towards respective measurement sites;
an antenna;
a transceiver circuit coupled to the antenna;
an AC to DC voltage transformation circuit coupled to the transceiver circuit and providing implant power supply from energy contained in an implant control signal received by the transceiver circuit;
a controller connected to the transceiver circuit and processing operation data contained in the implant control signal received by the transceiver circuit;
an electrode selection circuit connected to the electrode array, the electrode selection circuit having selectable outputs for communication with selected ones of the electrodes and the respective measurement sites; and
a monitoring unit coupled between the controller and the electrode selection circuit, and controllably taking signal measurements at the selected ones of the measurement sites in response to monitoring control signals and producing test result signals indicative of the signal measurements;

the controller having a decoder circuit decoding the operation data contained in the implant control signal, a monitoring command generator decoding diagnosis instructions contained in the operation data and transmitting the monitoring control signals to the monitoring unit in accordance with the diagnosis instructions, and a diagnosis controller receiving and processing the test result signals from the monitoring unit.

21. The body implant according to claim 20, wherein the monitoring unit has a current and voltage measuring circuit measuring a current and a voltage across a monitored one of the measurement sites, a peak detector measuring a peak magnitude of the voltage, and a phase detector measuring a phase between the current and the voltage, the test result signals being derived from the current, the voltage and the phase.

22. The body implant according to claim 20, wherein the diagnosis controller is connected to the transceiver circuit, the test result signals being transmitted from the diagnosis controller to the transceiver circuit for emission out of the body implant depending on the operation data.

23. A body implant comprising:
an electrode array having multiple adjacent electrodes directed towards respective stimulation sites;
an antenna;
a transceiver circuit coupled to the antenna;
an AC to DC voltage transformation circuit coupled to the transceiver circuit and providing implant power supply from energy contained in an implant control signal received by the transceiver circuit;
a controller connected to the transceiver circuit and processing operation data contained in the implant control signal received by the transceiver circuit;
a stimuli generator circuit connected to the controller and generating stimulation signals in accordance with the operation data; and
an electrode selection circuit connected between the stimuli generation circuit and the electrode array, the electrode selection circuit having selectable outputs grouped into channels for transmission of the stimulation signals to selected ones of the electrodes in accordance with the operation data;
the electrode selection circuit including, for each channel, a demultiplexer circuit connected to and operating switch arragements in accordance with site and polarity control signals, the switch arrangements being subjected to the stimulation signals and connected respectively to the outputs assigned to the channel;
the stimuli generator circuit including, for each channel, a signal generator controlled by a channel controller assisted by a timer connected to a register circuit receiving stimulation control signals, the signal generator producing the stimulation signals in accordance with the stimulation control signals, the register circuit and the channel controller producing the site and polarity control signals in accordance with the stimulation control signals; and
the controller having a decoder circuit decoding the operation data contained in the implant control signal, a configuration controller storing stimulation parameters specified in the operation data, and a stimulation command controller transmitting the stimulation control signals to the stimuli generator circuit in accordance with the stimulation parameters.

24. The body implant according to claim 23, wherein each register circuit comprises first and second sets of registers, one of which being used to load the stimulation control signals for a next stimulation while the other one being used to provide the stimulation control signals for a current stimulation.

25. The body implant according to claim 23, wherein each signal generator comprises a digital to analog converter producing an analog current signal forming one of the stimulation signals.

26. The body implant according to claim 23, further comprising:
- a monitoring unit coupled between the controller and the electrode selection circuit, and controllably taking measurements of selected ones of the stimulation signals in response to monitoring control signals and producing test results signals indicative of the measurements;

and wherein;
- the electrode selection circuit further includes, for each channel, a multiplexer circuit connected to the outputs assigned to the channel for selective monitoring thereof by the monitoring unit depending on a monitoring channel signal; and
- the controller includes a monitoring command generator decoding diagnosis instructions contained in the operation data and transmitting the monitoring control signals to the monitoring unit and the monitoring channel signal to the electrode selection circuit in accordance with the diagnosis instructions, and a diagnosis controller receiving and processing the test result signals from the monitoring unit.

27. The body implant according to claim 26, wherein the monitoring unit comprises a peak detector measuring a highest amplitude level of a monitored one of the stimulation signals, and a comparator producing an overflow signal when the highest amplitude level exceed a predetermined safety threshold, the overflow signal being reported to the diagnosis controller for processing thereof.

* * * * *